(12) United States Patent
Dorshow et al.

(10) Patent No.: US 11,969,268 B2
(45) Date of Patent: *Apr. 30, 2024

(54) SYSTEMS AND METHODS FOR HOME TRANSDERMAL ASSESSMENT OF GASTROINTESTINAL FUNCTION

(71) Applicant: MediBeacon Inc., St. Louis, MO (US)

(72) Inventors: Richard B. Dorshow, St. Louis, MO (US); Steven J. Hanley, St. Louis, MO (US); Terence Stern, St. Louis, MO (US); James Harr, St. Louis, MO (US)

(73) Assignee: MEDIBEACON INC., St. Louis, MO (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/378,059

(22) Filed: Jul. 16, 2021

(65) Prior Publication Data

US 2022/0022820 A1    Jan. 27, 2022

Related U.S. Application Data

(60) Provisional application No. 63/056,070, filed on Jul. 24, 2020.

(51) Int. Cl.
*A61B 5/1455* (2006.01)
*A61B 5/00* (2006.01)
(52) U.S. Cl.
CPC ............ *A61B 5/742* (2013.01); *A61B 5/0064* (2013.01); *A61B 5/0071* (2013.01); *A61B 5/42* (2013.01);

(Continued)

(58) Field of Classification Search
CPC .............................. A61B 5/0071; A61B 5/42
See application file for complete search history.

(56) References Cited

U.S. PATENT DOCUMENTS 10,772,503 B2 *  9/2020  Raisoni ................ A61B 5/0022
11,197,625 B1 * 12/2021  Schleicher ............ A61B 5/681
(Continued)

FOREIGN PATENT DOCUMENTS

WO       2018145193 A1    8/2018

OTHER PUBLICATIONS

International Search Report and Written Opinion for PCT/US2021/41811, dated Nov. 14, 2021, 17 pages.

(Continued)

*Primary Examiner* — Marjan Fardanesh
(74) *Attorney, Agent, or Firm* — Armstrong Teasdale LLP

(57) ABSTRACT

Disclosed herein is a non-transitory computer-readable media having computer-executable instructions thereon. When executed by the processor of a mobile computing device, the computer-executable instructions cause the processor to wirelessly communicatively couple the mobile computing device to a GI sensor (optionally by displaying instructions on a pairing screen), display a sensor placement screen that instructs the user to place the GI sensor on a body of a patient, prompts the user to administer a GI agent into the body of the patient; transmit a signal from the mobile computing device to the GI sensor to cause the GI sensor to initiate collection of light absorbance data for calculating GI function of the patient; receive light absorbance data from the GI sensor, and store the received light absorbance data.

19 Claims, 10 Drawing Sheets

(52) U.S. Cl.
CPC .......... *A61B 5/7405* (2013.01); *A61B 5/7455* (2013.01); *A61B 2560/02* (2013.01)

(56) References Cited

U.S. PATENT DOCUMENTS

| | | | |
|---|---|---|---|
| 2008/0097188 | A1 | 4/2008 | Pool et al. |
| 2013/0303865 | A1* | 11/2013 | Rebec .................. A61B 5/0013 600/309 |
| 2014/0159912 | A1* | 6/2014 | Fraden ................... G16H 40/67 340/870.02 |
| 2014/0365142 | A1* | 12/2014 | Baldwin .............. A61B 5/0002 702/24 |
| 2016/0066894 | A1* | 3/2016 | Barton-Sweeney ......................... A61B 10/0012 600/301 |
| 2016/0113503 | A1 | 4/2016 | Benaron |
| 2017/0050006 | A1 | 2/2017 | Imran et al. |
| 2018/0214057 | A1* | 8/2018 | Schultz ................ A61B 5/7203 |
| 2019/0008450 | A1 | 1/2019 | Gurievsky et al. |
| 2019/0167902 | A1* | 6/2019 | Kamen .............. A61B 5/14532 |
| 2020/0033267 | A1* | 1/2020 | Klaiman ............ G01N 21/6458 |
| 2020/0090491 | A1* | 3/2020 | Fateh ..................... G08B 21/24 |
| 2020/0237282 | A1 | 7/2020 | Dorshow et al. |

OTHER PUBLICATIONS

Acurable; We Create Accurate and User Friendly Wearable Medical Devices Intended to be Used by Patients at Home; product page; 8 pgs; retrieved Sep. 16, 2020 from the Internet: https://acurable.com/.
Apple; Apple Watch Series 5—Technical Specifications; product page; 3 pgs; retrieved Sep. 15, 2020 from the Internet: https://support.apple.com/kb/SP808?viewlocale=en_US&locale=en_US.
Ava; The Ava Bracelet; product page; 5 pgs; retrieved Sep. 16, 2020 from the Internet: https://www.avawomen.com/how-ava-works/healthcare/technology/.
AWAK; AWAK; product page; 5 pgs; retrieved Sep. 16, 2020 from the Internet: https://awak.com/product/.
Beddr; Tune your Sleep with the SleepTuner; product page; 20 pgs; retrieved Sep. 16, 2020 from the Internet: https://www.beddrsleep.com/sleeptuner.
Biointellisense; New! BioButton COVID-19 Screening Solution; product page; 12 pgs; retrieved Sep. 16, 2020 from the Internet: https://biointellisense.com/biobutton.
Biovotion; Everion—Revealing Medical Grade Data You Can Act On; 3 pgs; retrieved Sep. 16, 2020 from the Internet: https://www.biovotion.com/everion/.
Dexcom; Dexcom Continuous Glucose Monitoring; product page; 10 pgs; retrieved Sep. 15, 2020 from the Internet: https://www.dexcom.com/g6/features-and-benefits.
Eccrine; Eccrine Systems, Inc. Sweatronics; product page; 4 pgs; retrieved Sep. 16, 2020 from the Internet: https://www.eccrinesystems.com/technology.
ESight; Meet eSight 4; product page; 11 pgs; retrieved Sep. 16, 2020 from the Internet: https://esighteyewear.com/low-vision-device-for-visually-impaired/.
Flextrapower; Smart Insole; product home page. 4 pgs; retrieved Sep. 15, 2020 from the Internet: https://www.flextrapower.com/products/#insole.
Matrix; PowerWatch; product page; 5 pgs; retrieved Sep. 15, 2020 from the Internet: https://www.powerwatch.com/products/powerwatch-2.
Medcomp; products Dignity CT Ports; product page; 1 pg; retrieved Sep. 15, 2020 from the Internet: http://www.medcompnet.com/products/ports/dignity_ct_ports.html.
Medtronic; InterStim II System; product page; 5 pgs; retrieved Sep. 15, 2020 from the Internet: https://www.medtronic.com/us-en/healthcare-professionals/products/urology/sacral-neuromodulation-systems/interstim-ii.html.
Medtronic; LINQ II; product page; 9 pgs; retrieved Sep. 15, 2020 from the Internet: https://www.medtronic.com/us-en/healthcare-professionals/products/cardiac-rhythm/cardiac-monitors/linq-ii.html.
Philips; Biointellisense Biosticker; product page; 8 pgs; retrieved Sep. 16, 2020 from the Internet: https://www.usa.philips.com/healthcare/services/population-health-management/patient-engagement/biointellisense-biosticker.
Proteus; Proteus Digital Health; product page; 4 pgs; retrieved Sep. 16, 2020 from the Internet: https://www.proteus.com/.
Sony; mSafety Technical Specifications; product page; 6 pgs; retrieved Sep. 16, 2020 from the Internet: https://iot.sonynetworkcom.com/msafety/technology.
Vivalnk; Fever Scout; product page; 7 pgs; retrieved Sep. 16, 2020 from the Internet: https://www.vivalnk.com/feverscout.
Vivalnk; Medical Sensor Platform; product page; 5 pgs; retrieved Sep. 16, 2020 from the Internet: https://www.vivalnk.com/product/platform.
Vivalnk; Wellness Quantified Vital Scout; product page; 6 pgs; retrieved Sep. 16, 2020 from the Internet: https://www.vivalnk.com/vitalscout.
Withings; Hybrid Smartwatches; product home page; 13 pgs; retrieved Sep. 16, 2020 from the Internet: https://www.withings.com/us/en/watches.
Zimmer Biomet; mymobility; product page; 9 pgs; retrieved Sep. 15, 2020 from the Internet: https://www.zimmerbiomet.com/medical-professionals/zb-connect/mymobility.html.

* cited by examiner

Figure 2
Bluetooth Pairing
Establish a Bluetooth connection with the transdermal sensor:
- Remove sensor from packaging
- Activate the Bluetooth feature on the sensor by pressing logo on top of sensor 
- Press "Connect" once the sensor is in pairing mode
CONNECT
- Screen will indicate when devices are paired
Solid wifi icon indicates the devices are paired

Figure 3

Transdermal Sensor Placement

- The sensor can either be placed on your sternum or upper chest
- Select the target location by ensuring that the location is flat and color of the skin is uniform
- Remove hair from the area where the sensor will be placed
- Sterilize the area with the swab
- Remove liner from the back of the transdermal sensor by pulling on the blue tab 
- Place transdermal sensor directly on the skin of the prepped area
- Once sensor is positioned press

NEXT

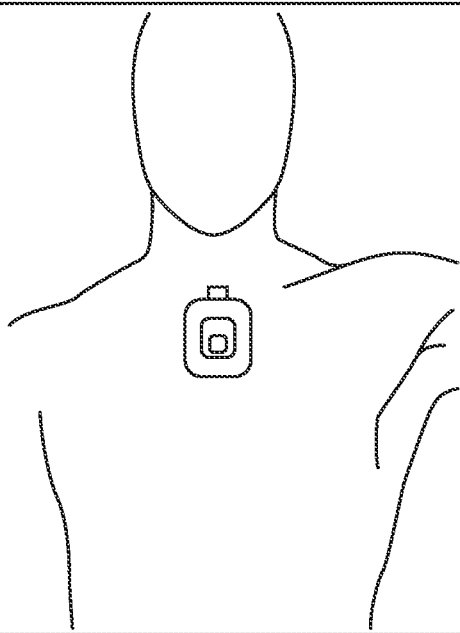

Figure 7

Results

- Results can be sent directly to your physician by pressing TRANSMIT

In order to ensure the accuracy, the Transdermal GI Permeability Measurement can only be used once every 24 hours

Transdermal GI Permeability Measurement

Displayed Measurement Reading

SYSTEMS AND METHODS FOR HOME TRANSDERMAL ASSESSMENT OF GASTROINTESTINAL FUNCTION

CROSS-REFERENCE TO RELATED APPLICATION

This application claims priority benefit of U.S. Provisional Application Ser. No. 63/056,070 filed Jul. 24, 2020, the entire contents of which are incorporated by reference herein.

FIELD OF INVENTION

The field of the disclosure relates generally to a computer program and system for facilitating home medical care. More specifically, this disclosure relates to assessing gastrointestinal function in a patient outside of a clinical or hospital setting using a mobile computing device and a system for performing the same.

BACKGROUND

In the clinical and preclinical field, determining various organ functions is accorded great importance since, for example, corresponding therapies or medications can be controlled in accordance with said organ functions.

Gastrointestinal (GI) mucosal integrity is a major challenge facing clinical medicine. Proper functioning of the intestines depends on the mucosa having sufficient surface capacity with which to absorb nutrients as well as having sufficient structural integrity to maintain the barrier function of the lining of this organ. In multiple inflammatory conditions, including Crohn's Disease, celiac disease, type 1 diabetes, graft-versus-host disease (GvHD), non-alcoholic fatty liver disease, multiple organ system failure in intensive care unit patients, and infections with human immunodeficiency virus, this barrier function is disrupted.

Various molecular strategies to probe the structure and function of the small bowel have been developed. The chief goal of all of these strategies is to directly or indirectly assess the structural integrity of the intestinal epithelium, which is comprised of a carpet of highly specialized columnar epithelial cells joined by tight junctions and adherens junctions. Molecules are selected to probe the competency of uptake and of permeability. Generally, integrity lesions that result in increased passive diffusion across the mucosa are detected by challenging a host with a substance that is not found in the diet, and assessing its uptake and/or clearance by studying the blood and the urine. In this model, uptake and excretion are abnormal. Conversely, GI transport capacity is assessed by administering a challenge substance that is easily absorbed in health and disease, but where uptake is limited by surface availability (as would be hindered in anatomic short gut or diminished villous surface area). Such substances are then measured in the urine and blood, and uptake reflects a gut of appropriate mass.

The most widely used test is termed the lactulose to mannitol ratio (L:M). Sugars (i.e., lactulose and mannitol) are administered orally, and their excretion is measured in the urine. The basis for the test lies in their two differential molecular weights. The larger sugar, lactulose, MW=342, is minimally absorbed during transit through an intact gut lined by intact epithelial, with highly competent tight junction functionality, and this disaccharide is therefore considered nearly impermeant. The smaller sugar, mannitol (MW=182), in contrast, is assimilated by an intact as well as an injured (permeant) gut via transcellular pathways and this absorption is proportional to the absorptive capacity of the gut. Both sugars distribute throughout the body in a hydrophilic compartments, and are then cleared by glomerular filtration. They are then measured in tandem in the urine. The co-administration, and the use of ratios in the urine, obviate single molecule assessments, because the ratio is independent of gastric emptying, or partial vomiting of the challenge sugars. Other sugars have been used to measure small and large bowel permeability, and include rhamnose and sucralose and D-xylose.

Measurements of challenge substances can be technically difficult. If peak or repeated circulating values are sought, phlebotomy is required, and there are assumptions about the kinetics of the peak. A urine collection is less invasive, but usually occurs over multiple hours, and is cumbersome to perform. An indirect test, such as measuring bacterial metabolism reflecting undigested sugar, requires specialized equipment. Hence, specimen acquisition, handling, and analysis are all very critical, but difficult to perform, and require medical personnel and facilities for collection.

Many patients with impaired gut function also suffer from numerous other medical difficulties and may have limited or impaired mobility. In some instances, patients are home-bound and receiving medical care from a home health provider such as a nurse. It can be difficult for these patients to travel to a hospital or clinical location for medical assessment. The patients most in need of accurate and timely assessment may have the greatest difficulty in getting that assessment. Thus, there is a need for assessing the GI function of a patient without requiring the patient to travel to a hospital or clinical location for the assessment.

BRIEF DESCRIPTION

In one aspect, disclosed herein is a non-transitory computer-readable media having computer-executable instructions thereon, wherein when executed by at least one processor of a mobile computing device, cause the at least one processor of the mobile computing device to wirelessly communicatively couple the mobile computing device to a sensor, display a sensor placement screen that instructs the user to place the sensor on a body of a patient, prompt the user to administer a fluorescent GI agent into the body of the patient, transmit a signal from the mobile computing device to the sensor to cause the sensor to initiate collection of light absorbance data for calculating GI function of the patient, receive light absorbance data from the sensor, and store the received light absorbance data.

In another aspect, disclosed herein is a computer-implemented method for assessing GI function in a patient. The method is implemented using a mobile computing device that includes at least one processor in communication with at least one memory, and at least one user interface. The method includes displaying a sensor placement screen that instructs the user to place a sensor on the body of the patient, communicatively coupling the sensor on the body of the patient to the mobile computing device (optionally by displaying instructions on a pairing screen), prompting the user to administer a fluorescent GI agent into the body of the patient, transmitting a signal from the mobile computing device to the sensor, the signal causing the sensor to collect the light absorbance data, and displaying a measurement screen that instructs the user to wait a predetermined period of time while the sensor collects light absorbance data.

In yet another aspect, disclosed herein is a system for assessing GI function in a patient. The system generally includes a mobile computing device having installed thereon a computer program for assisting a user in assessing GI function in the patient, a sensor configured to be wirelessly communicatively coupled to the mobile computing device, and a fluorescent GI agent.

In yet another aspect, disclosed herein is a kit for assessing GI function. The kit includes a fluorescent GI agent configured to emit at least one response light in response to the electromagnetic radiation generated by a sensor; a sensor configured to attach to the body of the patient, emit electromagnetic radiation in the direction of the body of the patient, and detect at least one response light emitted by the GI agent inside the body of the patient in response to the electromagnetic radiation; and a mobile computing device wirelessly communicatively coupled to the sensor and programmed to receive response light data from the sensor and calculate the GI function of the patient based on the response light data.

BRIEF DESCRIPTION OF THE DRAWINGS

The Figures described herein depict various aspects of the systems and methods disclosed therein. It should be understood that each Figure depicts an embodiment of a particular aspect of the disclosed systems and methods, and that each of the Figures is intended to accord with a possible embodiment thereof.

FIG. 2 is an example screenshot of a Bluetooth pairing screen for the software application that instructs the patient to communicatively couple a mobile computing device with a sensor in accordance with the present disclosure.

FIG. 3 is an example screenshot of a sensor placement screen for the software application that instructs the patient how and where to place the sensor on their body.

FIG. 7 is an example screenshot of a results screen for the software application that displays a final GI permeability measurement, and enables the patient to transmit the final GI permeability measurement to his or her health care provider.

DETAILED DESCRIPTION

Figure 1:
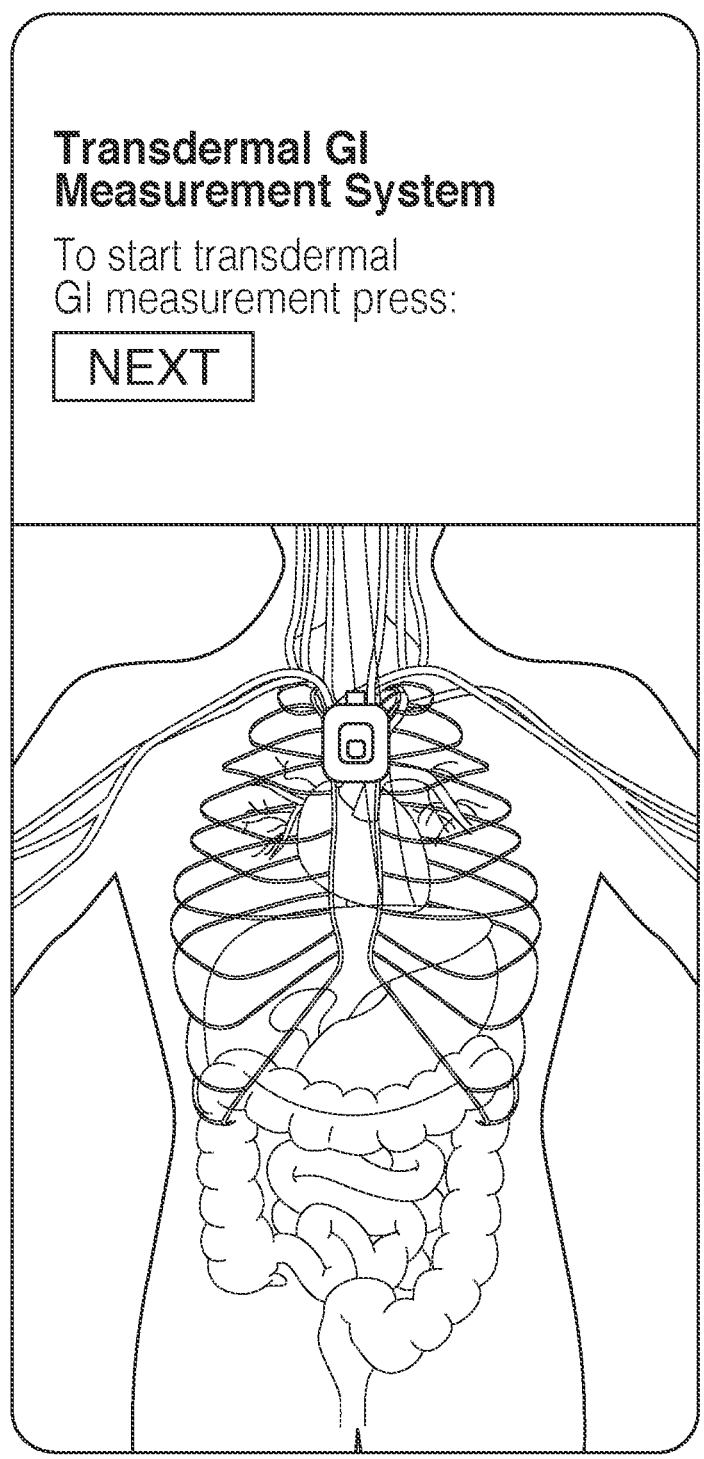
FIG. 1 is an example screenshot of a home screen for a software application used to assess the GI function in a patient in accordance with the present disclosure.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The computer-implemented methods discussed herein may include additional, less, or alternate actions, including those discussed elsewhere herein. The methods may be implemented via one or more local or remote processors, transceivers, servers, and/or sensors, and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

As will be appreciated based upon the specification, the described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, e.g., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program (i.e., a software application) is provided, and the program is embodied on a computer readable medium. In an exemplary embodiment, the program is executed on a single computer system. In a further embodiment, the computer system is a mobile computing device such as a smartphone or a tablet, or any other portable device capable of storing and processing data as described herein. The computer program is flexible and designed to run in various different environments without compromising any major functionality. Nonlimiting examples of different computing environments include smartphones running either the iOS or Android operating systems.

A computer program (i.e., a software application installed on a non-transitory computer-readable medium) and system are described hereinafter substantially with regard to GI function monitoring. In principle, however, other applications are also conceivable in which the function of a particular organ can be detected by means of determining a temporal profile of an indicator sub stance.

At a high level, provided herein is a computer program and a sensor configured to attach to the skin of a patient. The computer program is designed to run on a mobile computing device and the sensor (also referred to herein as a GI sensor) is designed to be in wireless communication with the computer program (e.g., via a Bluetooth connection). The patient attaches the sensor to their body, e.g., on the skin, and, after the sensor is calibrated and customized to the patient's unique skin tone and physiological characteristics, the patient then administers to him or herself a fluorescent agent (also referred to as an indicator substance). The agent is configured to emit light in response to electromagnetic radiation emitted by the sensor. A detector on the sensor then detects the emitted light over a period of time and transmits information about the detected light to the mobile computing device running the computer program. Information transmitted can include, but is not limited to, detected light intensity and a time when the light intensity is detected. This information is then used by the computer program to transdermally assess a particular vital physiological function of the patient. The transdermal measurement of the particular vital physiological function may then be displayed on an interface of the mobile computing device. Additionally or alternatively, the transdermal measurement may be transmitted from the mobile computing device to a health care provider of the patient. This system for assessing a particular physiological function of the patient is designed to be operated outside of a hospital or health care provider's office. For example, it may be operated by the patient in their own residence.

In various aspects, the assessment of physiological function may take place partially in a health care provider's office and/or hospital and partially in a patient's own residence or other non-clinical setting. The health care provider's office may be set up for physiological function evaluation of the patient. In this aspect, the health care provider may connect the sensor to the patient, with the sensor in wired or wireless communication with the office's computer system. The health care provider may then enter patient information into the office's computer system that then also transfers to the sensor. The health care provider may initiate the sensor and wait a period of time for the sensor to automatically adjust to compensate for variation in individual differences in skin properties, as further described herein. Once a baseline is reached, the health care provider may administer the fluorescent agent to the patient and wait a first predetermined period of time (based on the physiological condition being assessed and potentially anticipated initial results) before disconnecting the sensor from the office's computer system (but not from the patient). The patient may then be allowed to move freely for a second predetermined period of time, which may include leaving the health care provider's office, until the measurement is complete. This may be shown by an indicator on the sensor or instructions from the health care provider. Data collected during the measurement period may be stored on the sensor or may be wirelessly communicated to the health care provider's office. The patient may then return to the health care provider's office, wherein the sensor is reconnected to the office's computer system, either before or after removing the sensor from the patient. The connection may be wired or wireless. If the data is stored on the sensor, rather than wirelessly transmitted, then the data is transferred to the office's computer system where the data is further processed and analyzed by the health care provider.

The system and methods of the present invention may be used to assess various physiological functions including but not limited to gastrointestinal (GI) function, kidney function (through measurement of glomerular filtration rate (GFR)), ocular abnormalities, and brain barrier function. In an exemplary embodiment, the systems and methods of the present invention may be used to assess GI function. GI functions that may be assessed include but are not limited to permeability of the GI tract (e.g. Crohn's disease, celiac disease, graft versus host disease, irritable bowel syndrome, and irritable bowel disease), gastric emptying and mucosal healing.

FIGS. 1 to 8 illustrate example screen shots of a user interface of the software application in accordance with the example embodiments of the present disclosure. The screen shots are displayed on a mobile computing device executing the software application. More specifically, FIG. 1 is an example screenshot of a home screen displayed on the mobile computing device. In the example embodiment, the home screen is the first screen displayed to the user when accessing the software application on the mobile computing device. The home screen instructs the user to proceed to the next step. Additional functionality, not shown, can be incorporated on this screen or on additional screens of the program. Additional functionality can include, but is not limited to, information such as patient identification information, insurance information, and/or contact information for the patient or the patient's health care provider (HCP). This, or any additional screen of the application, can also include a "Help" functionality in order to further instruct the patient or answer questions with respect to the operation and results of the procedure.

In the exemplary embodiment, the patient (for whom the GI function measurement is to be obtained) accesses and uses the software application on the mobile computing device. Alternatively, a user other than the patient (e.g., an in-home care giver) may access and use the software application to obtain a GI function measurement for the patient.

FIG. 2 is an example screenshot of an optional embodiment of the invention, wherein a Bluetooth pairing screen is displayed for the software application. As shown in FIG. 2, the Bluetooth pairing screen instructs the patient (or other user) to "pair" or communicatively couple the mobile computing device to a sensor. Pairing can be done using, for example, Bluetooth and/or any other suitable form of wireless communication between the mobile computing device and the sensor. Pairing can incorporate security features, such as requiring the user to enter a unique sensor identification number into the software application (e.g., using an input interface of the mobile computing device) to enable the pairing. In some aspects, no identification is required, and the pairing instead relies on the limited range of Bluetooth technology and proximity of the sensor to the mobile computing device. In another embodiment of the invention, the mobile computing device is automatically paired to a sensor.

In one embodiment, for example, once the software application is initialized on the mobile computing device, the software application causes the mobile computing device to automatically search for and attempt to pair with a sensor. In such embodiments, before completing pairing with a candidate sensor, the software application may prompt the user to verify that candidate sensor is the correct sensor. The verification may be provided, for example, through an encrypted data stream.

FIG. 3 is an example screenshot of a sensor placement screen for the software application. As shown in FIG. 3, the sensor placement screen instructs the patient to place the GI sensor on their skin. The GI sensor can be placed in any suitable location on the body of the patient, although, in some aspects, the patient is instructed to place the sensor in a specific spot, for example the sternum or pectoralis major. Additional instructions can be included with this, or an additional, screen of the computer program. In this example, the patient is also instructed regarding how to select a location on their skin for the sensor, and how to prepare and sterilize the location in order to achieve an optimal attachment of the sensor. Additionally, the screen also includes a selectable icon (e.g., a button) for the patient to confirm that the sensor has been placed properly on their skin. This prevents the computer program from moving on to the next step of the procedure until the sensor has been placed properly. Additional functionality can be incorporated into this, or any additional, screen of the computer program. In some aspects, the instructions illustrated in FIG. 3 are split between two or more screens.

Figure 4:
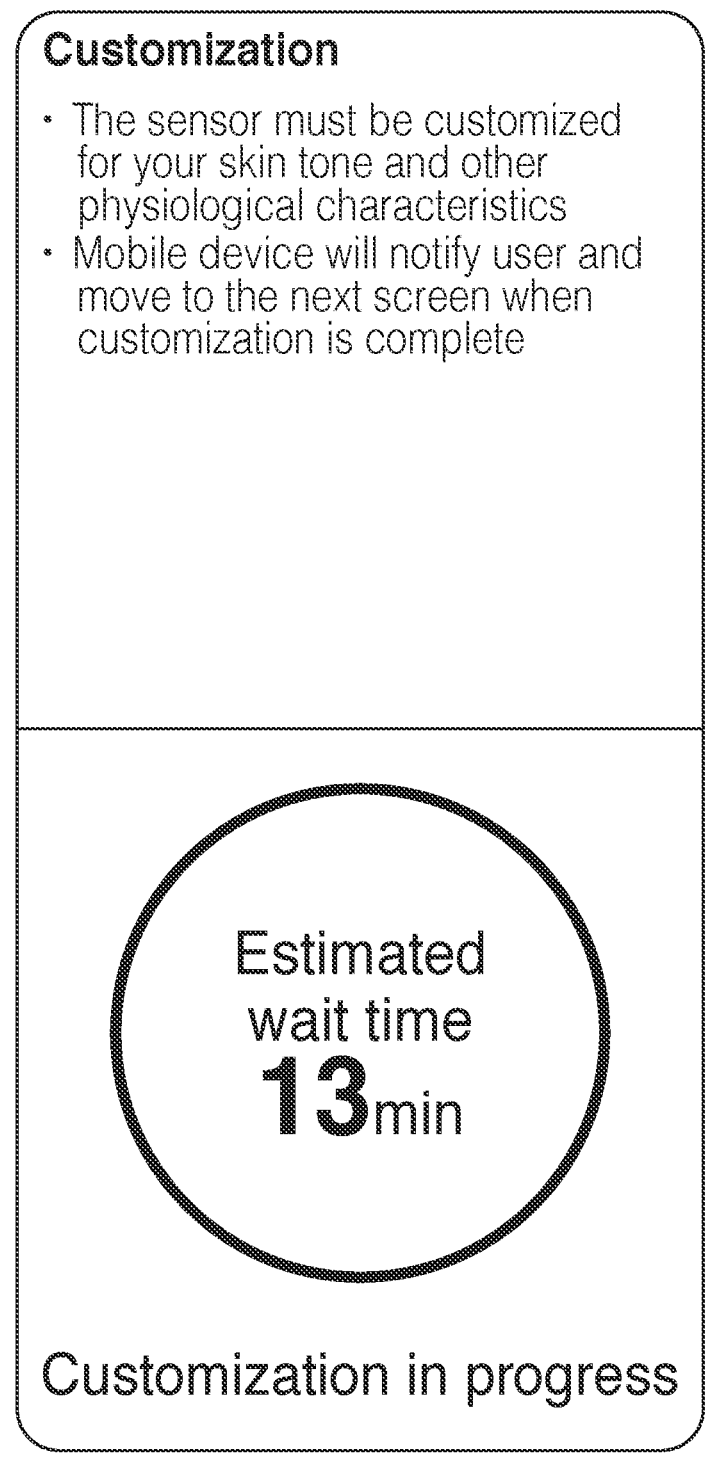
FIG. 4 is an example screenshot of a customization screen for the software application that instructs the patient to customize the sensor to a skin tone or other physiological characteristic of the patient.

FIG. 4 is an example screenshot of a customization screen for the software application. As shown in FIG. 4, the customization screen instructs the patient to customize the sensor to the patient's own skin tone and/or other physiological characteristics. In this aspect, the sensor receives a signal from the mobile computing device instructing the sensor to initiate a customization process. The customization process may include collecting a background level of light absorbance that naturally emanates from the body of the patient. It may also include adjusting the light strength or detector sensitivity in the sensor to account for differing skin colors of different patients. For example, patients of different ethnic backgrounds may have different skin tones, and the sensor adjusts to account for the different skin tones. In some aspects, the customization screen includes a countdown timer informing the patient as to how long before customization is complete and the patient can proceed to the next step in the procedure.

Figure 5:
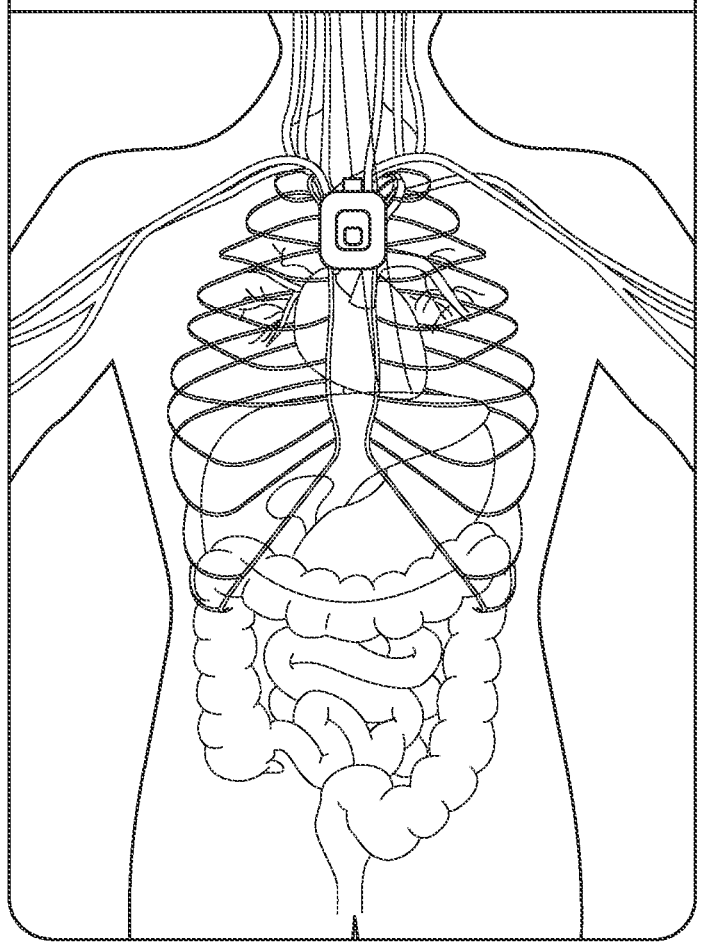
FIG. 5 is an example screenshot of an administration screen for the software application that instructs the patient to administer themselves a fluorescent GI agent.

FIG. 5 is an example screenshot of an administration screen for the software application. As shown in FIG. 5, the administration screen prompts and instructs the patient to administer to him or herself with a fluorescent GI agent detectable by the sensor. In some aspects, the patient is instructed to orally ingest a liquid or solid oral dosage form. In this aspect, the patient is also instructed that the sensor will communicate to the user through a signal such as a vibration, indicator light, or audio signal, when it detects the presence of the fluorescent GI agent inside the body of the patient. This informs the patient that the measurement has begun and that the fluorescent GI agent was properly administered. In other embodiments, the patient may be prompted to administer a second fluorescent GI agent detectable by the sensor.

In still other embodiments, the patient may be prompted to administer the fluorescent GI agent(s) using other techniques. For example, in one embodiment, to prompt the user, the mobile computing device vibrates to notify the user that the fluorescent GI agent should be administered. In another embodiment, to prompt the user, the mobile processing device transmits a control signal to the sensor to cause the sensor to generate an alert that notifies the user that the fluorescent GI agent should be administered. The alert generated by the sensor may be any suitable alert, including for example, an audible alert (e.g., generation of a particular sound), a visual alert (e.g., activation of an LED on the sensor), or a haptic alert (e.g., vibration of the sensor).

Figure 6:
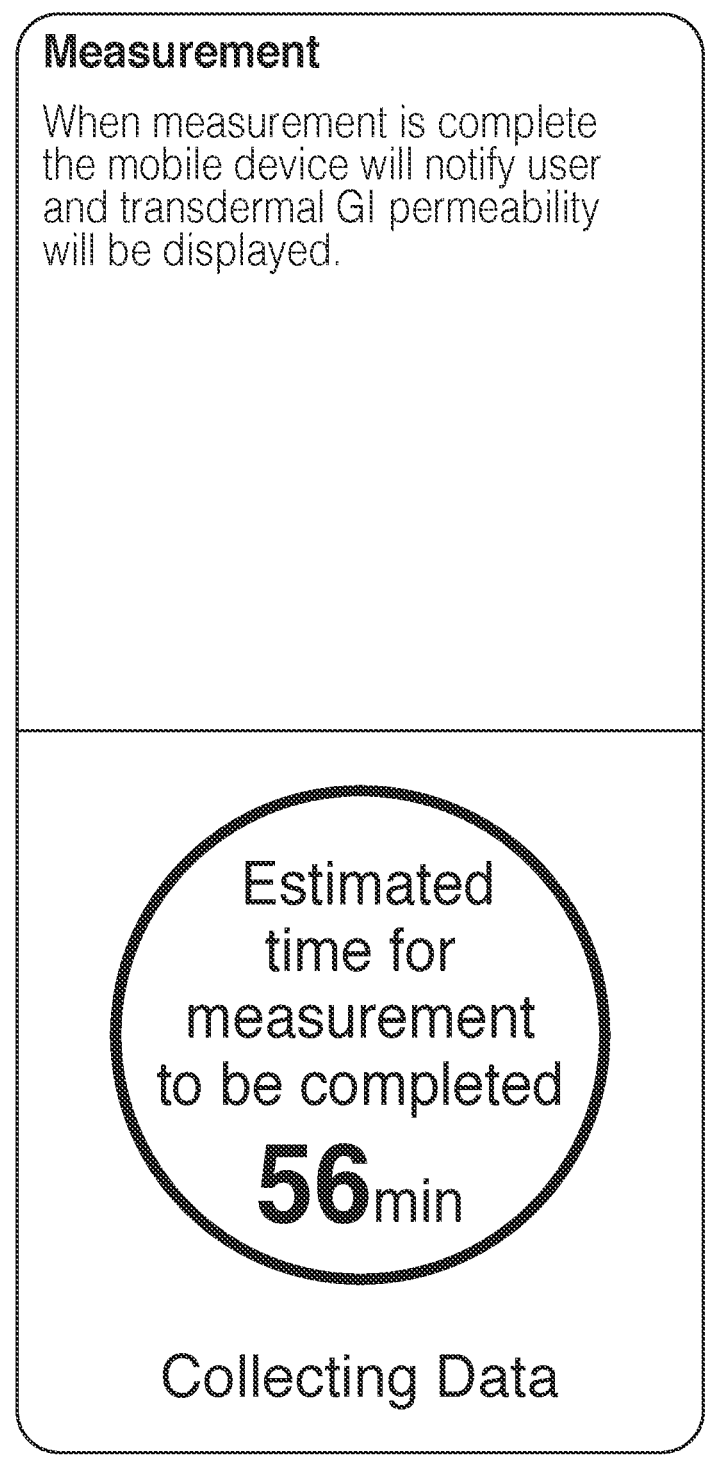
FIG. 6 is an example screenshot of a measurement screen for the patient application that provides feedback to the patient while the GI permeability is being determined.

FIG. 6 is an example screenshot of a measurement screen for the patient application. As shown in FIG. 6, the measurement of a GI permeability of the patient by the sensor proceeds without any additional action by the patient. In this aspect, the patient is informed that a predetermined amount of time must pass before the assessment is complete. Additionally, the computer program is configured such that the mobile computing device wirelessly receives data from the sensor during the assessment. In some aspects, the mobile computing device receives light absorbance data from the sensor, and the computer program uses the received light absorbance data to calculate the GI permeability measurement of the patient using mathematical algorithms included in the software application. For the measurement, the HCP of the patient may provide additional instructions as to what activities may or may not be permitted during the assessment. For example, the patient may be instructed that showering, bathing or strenuous exercise during the assessment is not permitted, but other routine activities are permitted. In some aspects, the computer program calculates an "initial" GI permeability measurement that is displayed on the screen of the mobile computing device part way through the assessment. This can be used to ensure that the sensor is properly collecting data while recognizing that light absorbance data collected over a longer period of time may be a more accurate assessment of the GI permeability of the patient.

FIG. 7 is an example screenshot of a results screen for the software application. As shown in FIG. 7, the final results of the GI permeability assessment are displayed on the screen of the mobile computing device. In some aspects, the patient is given the option to transmit the final results of the assessment from the mobile computing device to an HCP computing device associated with the HCP (e.g., by selecting a "TRANSMIT" button), while in other aspects, the computer program automatically causes the final results to be transmitted from the mobile computing device to the HCP computing device. Transmission of the results can be done using methods know in the art for transmitting data from one computing device to another. In the simplest example, the results can be transmitted by email from the patient's mobile computing device to the computing device of the HCP. Other transmission methods may also be used. In all aspects, because this is patient medical information, compliance with all laws regarding patient privacy is incorporated into this transmission. For example, the data may be encrypted before transmission from the mobile computing device to the computing device of the HCP.

Figure 8:
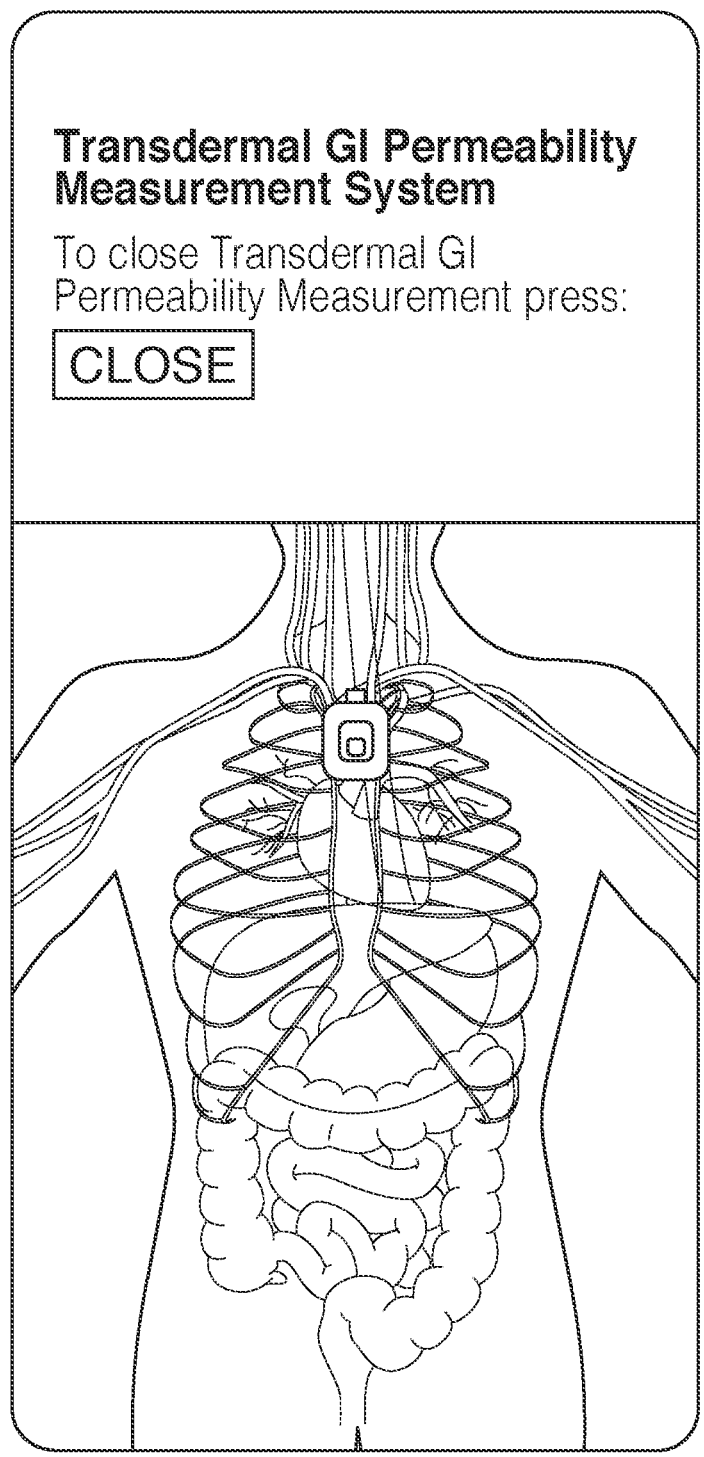
FIG. 8 is an example screenshot of an exit screen for the software application that enables the patient to exit the software application.

FIG. 8 is an example screenshot of an exit screen for the software application. As shown in FIG. 8, after completion of the assessment, the exit screen instructs the patient to close the software application. Additional instructions may be included here or on an additional screen. The patient may be instructed to remove the sensor from their body and/or how to dispose of it properly. In some aspects, the sensor may be reusable, and the patient is instructed how to properly remove and clean the sensor in preparation for reuse.

Figure 9:
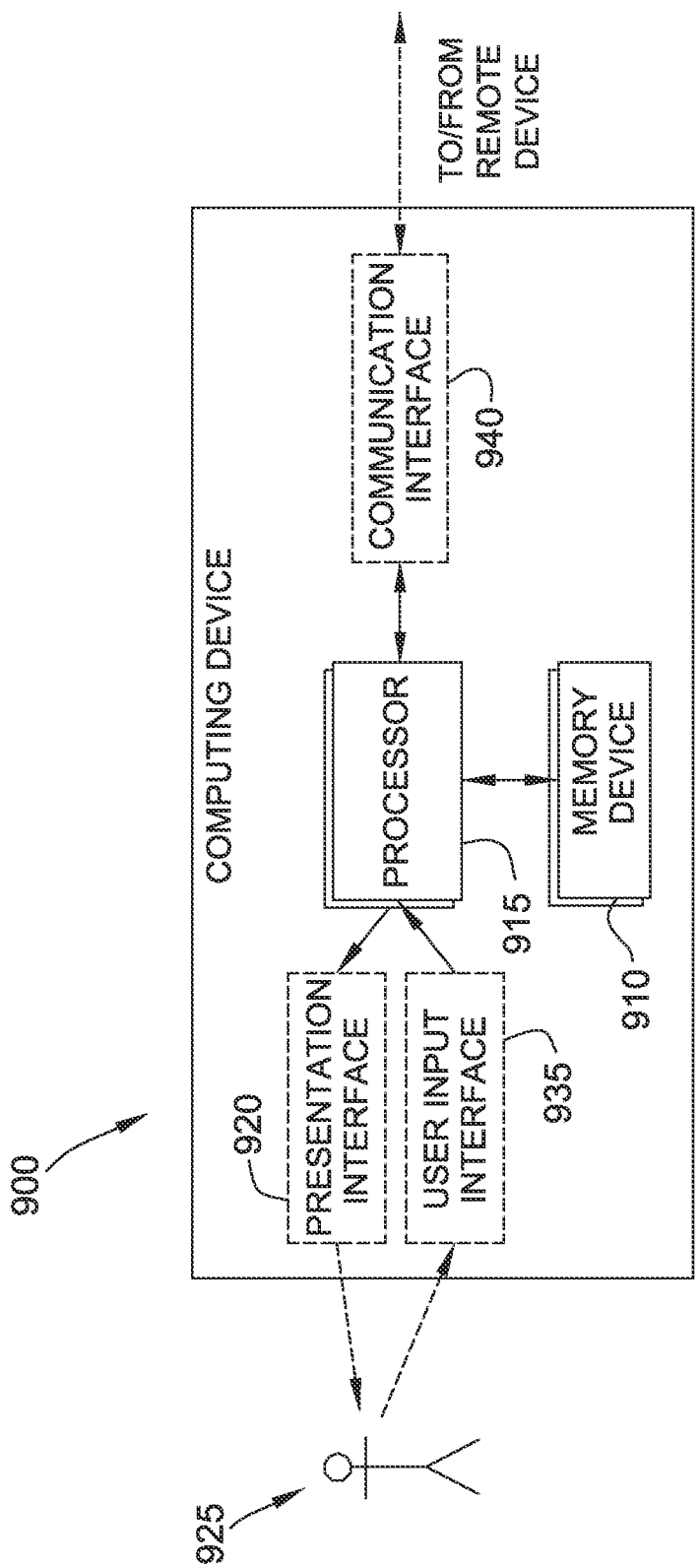
FIG. 9 is a block diagram of one embodiment of a computing device that may be used with the system shown in FIG. 10.

FIG. 9 is a block diagram of one embodiment of a computing device 900 that may be used to implement the mobile computing device operating the software application described herein. For example, computing device 900 may facilitate performing at least some of the functions described above.

Computing device 900 includes at least one memory device 910 and a processor 915 that is coupled to memory device 910 for executing instructions. In some embodiments, executable instructions are stored in memory device 910. Computing device 900 performs one or more operations described herein by programming processor 915. For example, processor 915 may be programmed by encoding an operation as one or more executable instructions and by providing the executable instructions in memory device 910.

Processor 915 may include one or more processing units (e.g., in a multi-core configuration). Further, processor 915 may be implemented using one or more heterogeneous processor systems in which a main processor is present with secondary processors on a single chip. As another illustrative example, processor 915 may be a symmetric multi-processor system containing multiple processors of the same type. Further, processor 915 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

Memory device 910 is one or more devices that enable information such as executable instructions and/or other data to be stored and retrieved. Memory device 910 may include one or more computer readable media, such as, without limitation, dynamic random access memory (DRAM), static random access memory (SRAM), a solid state disk, and/or a hard disk. The memory device 910 may be configured to store, without limitation, application source code, application object code, source code portions of interest, object code portions of interest, configuration data, execution events and/or any other type of data.

Computing device 900 includes a presentation interface 920 that is coupled to processor 915. Presentation interface 920 presents information to a user 925, such as the patient. For example, presentation interface 920 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 920 includes one or more display devices.

In the embodiment shown in FIG. 9, computing device 900 includes a user input interface 935. In this embodiment, user input interface 935 is coupled to processor 915 and receives input from user 925. User input interface 935 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 920 and user input interface 935.

Computing device 900 includes a communication interface 940 coupled to processor 915 in this embodiment. Communication interface 940 communicates with one or more remote devices. To communicate with remote devices, communication interface 940 may include, for example, a wired network adapter, a wireless network adapter, and/or a mobile telecommunications adapter.

Figure 10:
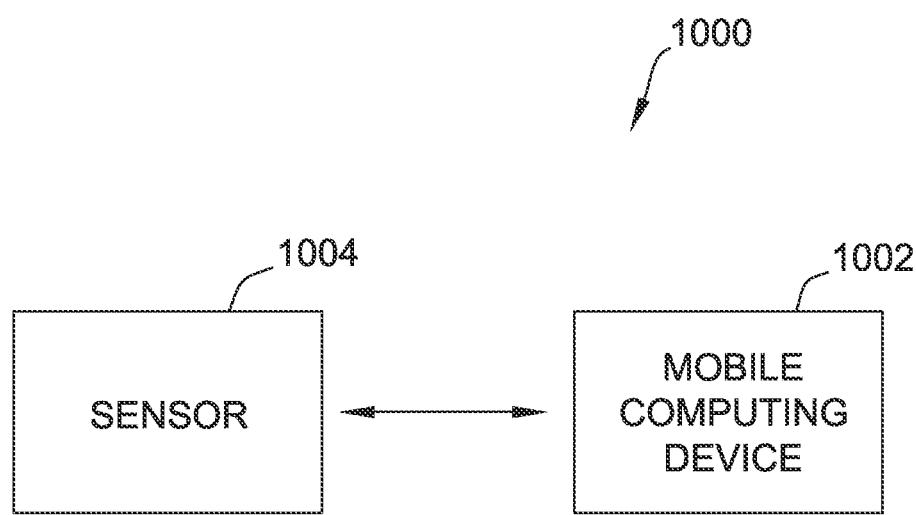
FIG. 10 is a block diagram of one embodiment of a system for home GI permeability monitoring.

FIG. 10 is a block diagram of a system 1000 for assessing the GI permeability in a patient. As illustrated in FIG. 10, the system generally includes a mobile computing device 1002 (e.g., computing device 900 (shown in FIG. 9)) communicatively coupled to a sensor 1004. As described above, mobile computing device 1002 executes a software application that assists a user in assessing GI permeability in the patient using sensor 1004. In some embodiments, disclosed herein is a non-transitory computer-readable media having computer-executable instructions thereon. When the instructions are executed by at least one processor of a mobile computing device it causes the at least one processor of the mobile computing device to display a pairing screen that instructs a user to wirelessly communicatively couple the mobile computing device to a sensor, display a sensor placement screen that instructs the user to place the GI sensor on a body of a patient, display an administration screen that instructs the user to administer a fluorescent GI agent into the body of the patient, transmit a signal from the mobile computing device to the GI sensor to cause the GI sensor to initiate collection of light absorbance data for calculating a GI permeability measurement of the patient, receive light absorbance data from the sensor, and store the received light absorbance data.

The system may optionally comprise additional components. For example, the system for assessing the GI function in a patient may further comprise a sensor. In some aspects, the sensor is as described elsewhere herein.

In some aspects, the instructions also cause the at least one processor to calculate the GI function of the patient using the light absorbance data. In some aspects, the instructions further cause the at least one processor to wirelessly transmit the GI function of the patient to a computing device of a health care provider. In some aspects, the instructions further cause the at least one processor to display a customization screen that instructs the patient to calibrate the sensor on the body of the patient, to transmit a signal from the mobile computing device to the sensor to initiate calibration of the sensor in response to receiving a user input to initiate sensor calibration, and to receive a signal from the sensor upon completion of sensor calibration. In some aspects, the computer-executable instructions further cause the processor of the mobile computing device to display an error message if an error occurs during execution of the instructions.

In still yet another aspect, disclosed herein is a computer-implemented method for assessing the GI function in a patient in need thereof. The method is implemented using a mobile computing device that comprises at least one processor in communication with at least one memory, and at least one user interface, and the method generally includes displaying a sensor placement screen that instructs the user to place a sensor on the body of the patient, communicatively coupling the sensor on the body of the patient to the mobile computing device (optionally by displaying instructions on a pairing screen), prompting the user to administer a fluorescent GI agent into the body of the patient, displaying a measurement screen that instructs the user on how to initiate collection of light absorbance data by the sensor, transmitting a signal from the mobile computing device to the sensor, the signal causing the sensor to collect the light absorbance data, displaying a collection screen that instructs the user to wait a predetermined period of time while the sensor collects the light absorbance data, and displaying a transmission screen that instructs the user on how to transmit the light absorbance data to a computing device of a health care provider.

In some aspects, the user is prompted to administer a first fluorescent GI agent into the body of the patient and a second fluorescent GI agent into the body of the patient. In this aspect, the first fluorescent GI agent is not substantially absorbed by a healthy gut and the second fluorescent GI agent is substantially absorbed by a healthy gut. GI function is assessed by comparing the detected fluorescence of the first fluorescent GI agent to the second fluorescent GI agent. The two fluorescent GI agents may possess different photophysical properties allowing for the simultaneous measurement of the fluorescence of the two agents. In another aspect, the location of disease or injury in the patient's gut, is assessed based on the time period between the detected fluorescence of each fluorescent GI agent and administration. Again, the two fluorescent GI agents may possess different photophysical properties allowing for the simultaneous measurement of the fluorescence of the two agents.

In still other aspects, the method further includes one or more of the following additional steps: displaying a customization screen that instructs the user on how to customize the sensor prior to collecting light absorbance data, calculating the GI function of the patient using the light absorbance data, displaying a results screen that displays the calculated GI function of the patient, waiting for patient/user input after each step in the computer implemented method indicating that the step was successfully completed, transmitting from the mobile computing device to a computing device of a health care provider the calculated GI function measurement, the light absorbance data, or both, and/or providing feedback to the user and/or patient if an error occurs at any time during execution of the method.

In still yet another aspect, disclosed herein is a kit for GI function assessment. The kit generally includes a fluorescent GI agent configured to emit at least one response light in response to the electromagnetic radiation generated by the sensor; a sensor configured to attach to the body of the patient, emit electromagnetic radiation in the direction of the body of the patient, and detect at least one response light emitted by the fluorescent GI agent inside the body of the patient in response to the electromagnetic radiation, a mobile computing device wirelessly communicatively coupled to the sensor and programmed to receive response light data from the sensor, and calculate the GI function of the patient based on the response light data. In some aspects, the fluorescent GI agent is as described elsewhere herein. In some aspects, the sensor is as described elsewhere herein. In some aspects, the mobile computing device is as described elsewhere herein.

In some aspects, the kit further comprises written instructions describing how to use the components of the kit in order to assess the GI function of the patient.

As used herein, the term "patient" and "user" may or may not refer to the same person. In some aspects, they are the same. In some aspects, they are different. When they are different, the user of the computer program is assisting the patient with the GI function assessment. For example, a home health nurse may assist a patient with the GI function assessment in the patient's own home thus saving the patient the difficulty of travelling to a doctor's office or hospital in order to have a GI function assessment performed. It is understood that the patient can be male or female, and that gendered pronouns used herein are used simply as a linguistic convenience.

As used herein, the term "not substantially absorbed" refers to agents that may be distinguished by the difference in their gut absorption in a healthy gut versus a diseased or injured gut. In some embodiments, not substantially absorbed into a healthy gut refers to less than 50%, less than 40%, less than 30%, less than 20%, less than 10%, less than 5%, or less than 1% of the administered amount is absorbed. In some such embodiments, the absorbed amount of the administered agent into a healthy gut is 0%, about 0.1%, about 0.5%, about 1%, about 5%, about 10%, about 15%, about 20% or about 25%, or any range constructed therefrom, such from 0% to about 25%, from 0% to about 20%, from 0% to about 15%, from 0% to about 10%, from 0% to about 5%, or from 0% to about 1%. In some embodiments, the amount of administered agent absorbed by a diseased or injured gut is at least 50%, at least 60%, at least 70%, at least 80%, at least 90%, at least 95%, at least at least 99%. In some such embodiments, the absorbed amount of the administered agent into a diseased or injured gut is 100%, about 99.9%, about 99.5%, about 99%, about 95%, about 90%, about 85%, about 80%, about 75%, about 70%, about 65%, about 60%, about 55%, or 50%, or any range constructed therefrom, such from 50% to 100%, from about 60% to 100%, from about 60% to about 90%, from about 70% to 100%, or from about 70% to about 90%. In some embodiments, agents within the scope of the present disclosure may be defined by a ratio of the administered amount absorbed into a diseased or injured gut to the administered amount absorbed into a healthy gut. In some such embodiments, the ratio is about 2:1, about 3:1, about 4:1 about 5:1, about 6:1, about 7:1, about 8:1, about 9:1, about 10:1, about 15:1, about 20:1, about 25:1, about 50:1, about 75:1, about 100:1, about 250:1, about 500:1, or about 1000:1, and any range constructed therefrom, such as from about 2:1 to about 1000:1, from about 2:1 to about 500:1, from about 2:1 to about 100:1, from about 2:1 to about 50:1, from about 5:1 to about 100:1, or from about 5:1 to about 50:1.

Examples of fluorescent GI agents (also referred to indicator substances and challenge molecules) suitable for use with the methods and devices herein include, but are not limited to, those disclosed in U.S. 62/577,951, U.S. Pat. Nos. 8,155,000, 8,664,392, 8,697,033, 8,703,100, 8,722,685, 8,778,309, 9,005,581, 9,283,288, 9,376,399, U.S. RE47, 413, U.S. RE47,255, U.S. Pat. Nos. 10,137,207, and 10,525, 149 which are all incorporated by reference in their entirety for all purposes.

In some aspects, the indicator substance is a pyrazine derivative of Formula I, or a pharmaceutically acceptable salt thereof,

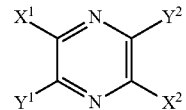

Formula I wherein each of $X^1$ and $X^2$ is independently selected from the group consisting of —CN, —CO$_2$R$^1$, —CONR$^1$R$^2$, —CO(AA), —CO(PS) and —CONH(PS); each of $Y^1$ and $Y^2$ is independently selected from the group consisting of —NR$^1$R$^2$ and

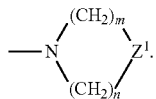

$Z^1$ is a single bond, —CR'R$^2$—, —O—, —NR$^1$—, —NCOR$^1$—, —S—, —SO—, or —SO$_2$—; each of R$^1$ to R$^2$ are independently selected from H, a polyol, and a substituted polyol. In some aspects, each of R$^1$ to R$^2$ are independently selected from the group consisting of H, —CH$_2$(CHOH)$_a$H, —CH$_2$(CHOH)$_a$CH$_3$, —CH$_2$(CHOH)$_a$CO$_2$H, —(CHCO$_2$H)$_a$CO$_2$H, —(CH$_2$CH$_2$O)$_c$H, —(CH$_2$CH$_2$O)$_c$CH$_3$, —(CH$_2$)$_a$SO$_3$H, —(CH$_2$)$_a$SO$_3$—, —(CH$_2$)$_a$SO$_2$H, —(CH$_2$)$_a$SO$_2$—, —(CH$_2$)$_a$NHSO$_3$H, —(CH$_2$)$_a$NHSO$_3$—, —(CH$_2$)$_a$NHSO$_2$H, —(CH$_2$)$_a$NHSO$_2$—, —(CH$_2$)$_a$PO$_4$H$_3$, —(CH$_2$)$_a$PO$_4$H$_2$—, —(CH$_2$)$_a$PO$_4$H$_2$—, —(CH$_2$)$_a$PO$_4$$^{3-}$, —(CH$_2$)$_a$PO$_3$H$_2$, —(CH$_2$)$_a$PO$_3$H—, and —(CH$_2$)$_a$PO$_3$$^{2-}$. (AA) comprises one or more amino acids selected from the group consisting of natural and unnatural amino acids, linked together by peptide or amide bonds, and each instance of (AA) may be the same or different than each other instance.

'a' is a number from 0 to 10, 'c' is a number from 1 to 100, and each of 'm' and 'n' are independently a number from 1 to 3. In another aspect, 'a' is a number from 1 to 10. In still yet another aspect, 'a' is 0, 1, 2, 3, 4, 5, 6, 7, 8, 9 or 10.

(AA) comprises a polypeptide chain including one or more natural or unnatural α-amino acids linked together by peptide bonds or natural or unnatural β-amino acid(s), linked together by peptide bonds, or combination of α- and β-amino acid(s), linked by peptide bonds. The peptide chain (AA) may be a single amino acid, a homopolypeptide chain or a heteropolypeptide chain, and may be any appropriate length. In some embodiments, the natural or unnatural amino acid is an α-amino acid. In yet another aspect, the α-amino acid is a D-α-amino acid or an L-α-amino acid. In a polypeptide chain that includes two or more amino acids, each amino acid is selected independently of the other(s) in all aspects, including, but not limited to, the structure of the side chain and the stereochemistry. For example, in some embodiments, the peptide chain may include 1 to 100 amino acid(s), 1 to 90 amino acid(s), 1 to 80 amino acid(s), 1 to 70 amino acid(s), 1 to 60 amino acid(s), 1 to 50 amino acid(s), 1 to 40 amino acid(s), 1 to 30 amino acid(s), 1 to 20 amino acid(s), or even 1 to 10 amino acid(s). In some embodiments, the peptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the polypeptide chain (AA) refers to a single amino (e.g., either aspartic acid or serine). In some embodiments, the polypeptide chain may include 1 to 100 β-amino acid(s), 1 to 90 β-amino acid(s), 1 to 80 β-amino acid(s), 1 to 70 β-amino acid(s), 1 to 60 β-amino acid(s), 1 to 50 β-amino acid(s), 1 to 40 β-amino acid(s), 1 to 30 β-amino acid(s), 1 to 20 β-amino acid(s), or even 1 to 10 β-amino acid(s). In some embodiments, a combination of α-amino acids and β-amino acids of the polypeptide chain may be included. In some embodiments, the α-amino acids of the polypeptide chain (AA) are selected from the group consisting of aspartic acid, asparagine, arginine, histidine, lysine, glutamic acid, glutamine, serine, and homoserine. In some embodiments, the α-amino acids of the polypeptide chain (AA) are selected from the group consisting of aspartic acid, glutamic acid, serine, and homoserine. In some embodiments, the amino acid is selected from the group consisting of D-alanine, D-arginine D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tryptophan, D-tyrosine, and D-valine. In some embodiments, the α-amino acids of the peptide chain (AA) are selected from the group consisting of arginine, asparagine, aspartic acid, glutamic acid, glutamine, histidine, homoserine, lysine, and serine. In some embodiments, the α-amino acids of the peptide chain (AA) are selected from the group consisting of aspartic acid, glutamic acid, homoserine and serine. In some embodiments, the peptide chain (AA) refers to a single amino acid (e.g., D-aspartic acid or D-serine).

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose). In yet another aspect, the polysaccharide chain is an amino sugar where one or more of the hydroxy groups on the sugar has been replaced by an amine group. The connection to the carbonyl group can be either through the amine or a hydroxy group.

Table 1 provides a non-limiting list of exemplary indicator substances. In at least one example, the indicator substance may be 3,6-diamino-2,5-bis{N-[(1R)-1-carboxy-2-hydroxyethyl]carbamoyl}pyrazine. In another example, the indicator substance may be N2,N5-bis(2,3-dihydroxypropyl)-3,6-bis[(S)-2,3-dihydroxypropylamino]pyrazine-2,5-dicarboxamide. In another example, the indicator substance may be 3,6-diamino-N2,N5-bis((2R,3S,4S,5S)-2,3,4,5,6-pentahydroxyhexyl)pyrazine-2-5-dicarboxamide. In another example, the indicator substance may be 3,6-diamino-N2,N5-di(2,5,8,11,14,17,20,23,26,29,32,35,38,41,44,47,50,53,56,59,62,65,68-tricosaoxaheptacontan-70-yl)pyrazine-2,5-dicarboxamide. In yet another example, the indicator substance may be (2R,2'R)-2,2'-((3,6-bis(((S)-2,3-dihydroxypropyl)amino)pyrazine-2,5-dicarbonyl)bis(azanediyl))bis(3-hydroxypropanoic acid). In still another example, the indicator substance may be 3,6-Bis(2,5,8,11,14,17,20,23,26,29,32,35-dodecaoxaheptatriacontan-37-ylamino)-N2,N5-di(2,5,8,11,14,17,20,23,26,29,32,35-dodecaoxaheptatriacontan-37-yl)pyrazine-2,5-dicarboxamide. In a further example, the indicator substance may be 3,6-Bis(2,5,8,11,14,17,20,23,26,29,32,35-dodecaoxaoctatriacontan-38-ylamino)-N2,N5-di(2,5,8,11,14,17,20,23,26,29,32,35-dodecaoxaheptatriacontan-37-yl)pyrazine-2,5-dicarboxamide. In yet another example, the indicator substance may be D-serine,N,N'-[[3,6-bis[[(2S)-2,3-dihydroxypropyl]amino]-2,5-pyrazinediyl]dicarbonyl]bis-. In an example, the indicator substance may be 3,6-diamino-N2,N5-di(2,5,8,11,14,17,20,23,26,29,32,35,38,41,44,47,50,53,56,59,62,65,68,71-tetracosaoxatriheptacontan-73-yl)pyrazine-2,5-dicarboxamide. In another example, the indicator substance may be 3,6-N,N'-Bis(2,3-dihydroxypropyl)-2,5-pyrazinedicarboxamide.

TABLE 1

Indicator Substances

| Code Name | Molecular Weight (Da) | Structure | Chemical Name |
|---|---|---|---|
| MB-102 | 372 | 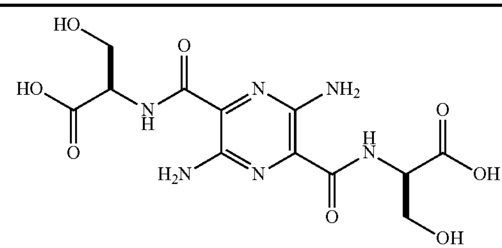 | 3,6-diamino-2,5-bis{N-[(1R)-1-carboxy-2-hydroxyethyl]carbamoyl}pyrazine |
| MB-404 | 492 | 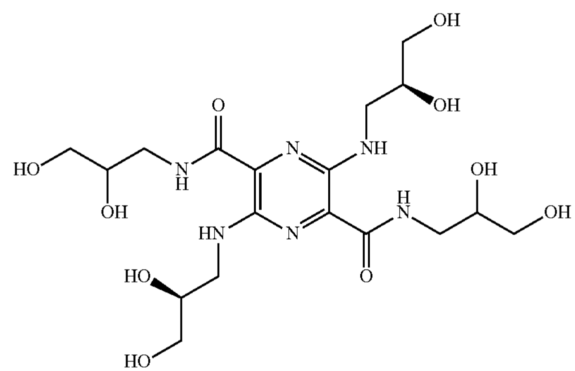 [SMILES: O=C(NCC(O)CO)c1nc(NC[C@H](O)CO)c(C(=O)NCC(O)CO)nc1NC[C@H](O)CO] | $N^2,N^5$-bis(2,3-dihydroxypropyl)-3,6-bis[(S)-2,3-dihydroxypropylamino]pyrazine-2,5-dicarboxamide |
| MB-106 | 524 | 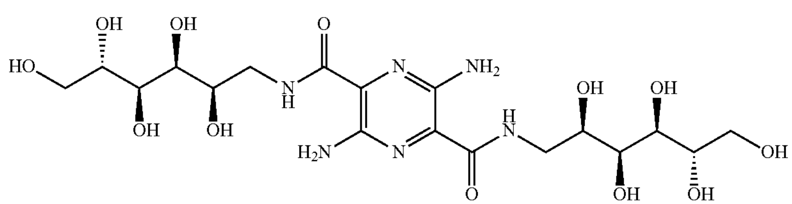 [SMILES: Nc1nc(C(=O)NC[C@@H](O)[C@H](O)[C@@H](O)[C@@H](O)CO)c(N)nc1C(=O)NC[C@@H](O)[C@H](O)[C@@H](O)[C@@H](O)CO] | 3,6-diamino-$N^2,N^5$-bis((2R,3S,4S,5S)-2,3,4,5,6-pentahydroxyhexyl)pyrazine-2-5-dicarboxamide |

TABLE 1-continued

Indicator Substances

| Code Name | Molecular Weight (Da) | Structure | Chemical Name |
|---|---|---|---|
| MB-216 | 2367 | 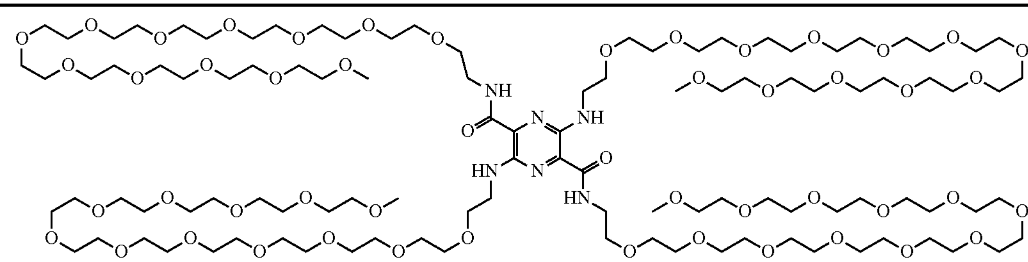 | 3,6-Bis(2,5,8,11,14,17,20,23,26,29,32,35-dodecaoxaheptatriacontan-37-ylamino)-N²,N⁵-di(2,5,8,11,14,17,20,23,26,29,32,35-dodecaoxaheptatriacontan-37-yl)pyrazine-2,5-dicarboxamide |
| MB-212 | 2395 | 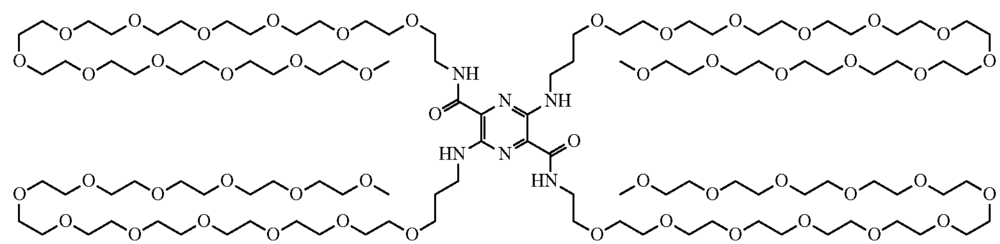 [SMILES: COCCOCCOCCOCCOCCOCCOCCOCCOCCOCCOCCOCCCNc1nc(C(=O)NCCOCCOCCOCCOCCOCCOCCOCCOCCOCCOCCOCCOC)c(NCCCOCCOCCOCCOCCOCCOCCOCCOCCOCCOCCOCCOC)nc1C(=O)NCCOCCOCCOCCOCCOCCOCCOCCOCCOCCOCCOCCOC] | 3,6-Bis(2,5,8,11,14,17,20,23,26,29,32,35-dodecaoxaoctatriacontan-38-ylamino)-N²,N⁵-di(2,5,8,11,14,17,20,23,26,29,32,35-dodecaoxaheptatriacontan-37-yl)pyrazine-2,5-dicarboxamide |
| MB-116 | 2250 | 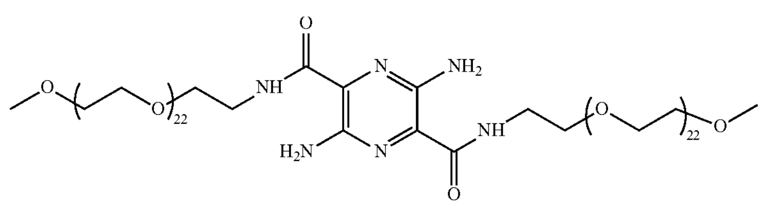 | 3,6-diamino-N²,N⁵-di(2,5,8,11,14,17,20,23,26,29,32,35,38,41,44,47,50,53,56,59,62,65,68-tricosaoxaheptacontan-70-yl)pyrazine-2,5-dicarboxamide |

TABLE 1-continued
Indicator Substances
| Code Name | Molecular Weight (Da) | Structure | Chemical Name |
|---|---|---|---|
| MB-206 | 520 | 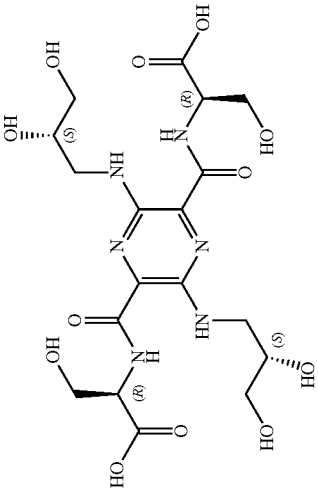 | D-Serine,N,N'-[[3,6-bis[[(2S)-2,3-dihydroxypropyl]amino]-2,5-pyrazinediyl]dicarbonyl]bis- |
| MB-112 | 2339 | 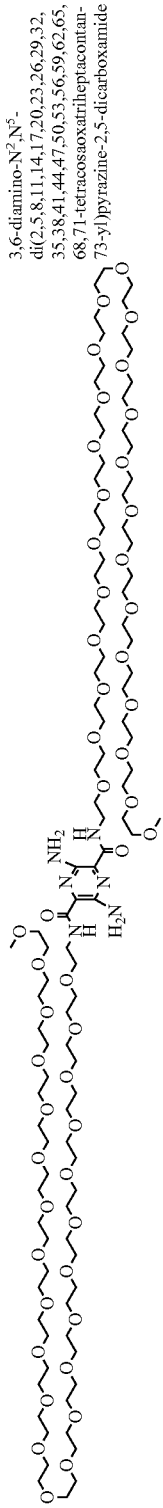 | 3,6-diamino-$N^2,N^5$-di(2,5,8,11,14,17,20,23,26,29,32,35,38,41,44,47,50,53,56,59,62,65,68,71-tetracosaoxatriheptacontan-73-yl)pyrazine-2,5-dicarboxamide |
| MB-402 | 344 | 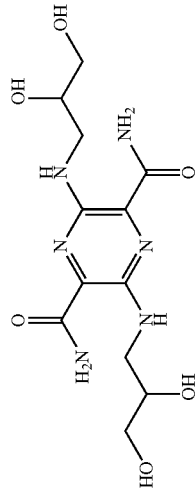 | 3,6-N,N'-Bis(2,3-dihydroxypropyl)-2,5-pyrazinedicarboxamide |

Other examples of fluorescent GI agents include, but are not limited to, 3,6-diamino-$N^2,N^2,N^5,N^5$-tetrakis(2-methoxyethyl)pyrazine-2,5-dicarboxamide, 3,6-diamino-$N^2,N^5$-bis(2,3-dihydroxypropyl)pyrazine-2,5-dicarboxamide, (2S,2'S)-2,2'-((3,6-diaminopyrazine-2,5-dicarbonyl)bis(azanediyl))bis(3-hydroxypropanoic acid), 3,6-bis(bis(2-methoxyethyl)amino)-$N^2,N^2,N^5,N^5$-tetrakis(2-methoxyethyl) pyrazine-2,5-dicarboxamide bis(TFA) salt, 3,6-diamino-$N^2,N^5$-bis(2-aminoethyl)pyrazine-2,5-dicarboxamide bis(TFA) salt, 3,6-diamino-$N^2,N^5$-bis(D-aspartate)-pyrazine-2,5-dicarboxamide, 3,6-diamino-$N^2,N^5$-bis(14-oxo-2,5,8,11-tetraoxa-15-azaheptadecan-17-yl) pyrazine-2,5-dicarboxamide, 3,6-diamino-$N^2,N^5$-bis(26-oxo-2,5,8,11,14,17,20,23-octaoxa-27-azanonacosan-29-yl) pyrazine-2,5-dicarboxamide, 3,6-diamino-$N^2,N^5$-bis(38-oxo-2,5,8,11,14,17,20,23,26,29,32,35-dodecaoxa-39-azahentetracontan-41-yl)pyrazine-2,5-dicarboxamide, bis(2-(PEG-5000)ethyl) 6-(2-(3,6-diamino-5-(2-aminoethylcarbamoyl) pyrazine-2-carboxamido) ethylamino)-6-oxohexane-1,5-diyldicarbamate, (R)-2-(6-(bis(2-methoxyethyl)amino)-5-cyano-3-morpholinopyrazine-2-carboxamido)succinic acid, (2R,2'R)-2,2'-((3,6-diaminopyrazine-2,5-dicarbonyl)bis(azanediyl))bis(3-hydroxypropanoic acid), (2S,2'S)-2,2'-((3,6-diaminopyrazine-2,5-dicarbonyl)bis(azanediyl))bis(3-hydroxypropanoic acid), (2R,2'R)-2,2'-((3,6-diaminopyrazine-2,5-dicarbonyl)bis(azanediyl))dipropionic acid, 3,3'-((3,6-diaminopyrazine-2,5-dicarbonyl)bis(azanediyl))dipropionic acid, 2,2'4(3,6-diaminopyrazine-2,5-dicarbonyl)bis(azanediyl))diacetic acid, (2S,2'S)-2,2'-((3,6-diaminopyrazine-2,5-dicarbonyl)bis(azanediyl)) dipropionic acid, 2,2'-((3,6-diaminopyrazine-2,5-dicarbonyl)bis(azanediyl))bis(2-methylpropanoic acid), and 3,6-diamino-N2,N5-bis((1R,2S,3R,4R)-1,2,3,4,5-pentahydroxypentyl) pyrazine-2,5-dicarboxamide.

In some aspects, the fluorescent GI agent is (2R,2'R)-2,2'-((3,6-diamino-pyrazine-2,5-dicarbonyl)bis(azanediyl))bis(3-hydroxypropanoic acid) (also known as MB-102 or 3,6-diamino-$N^2,N^5$-bis(D-serine)-pyrazine-2,5-dicarboxamide),

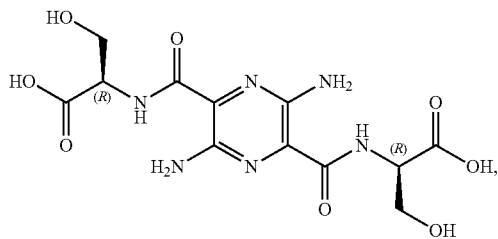

or a pharmaceutically acceptable salt thereof.

In some aspects, the fluorescent GI agent is (2S,2'S)-2,2'-((3,6-diamino-pyrazine-2,5-dicarbonyl)bis(azanediyl))bis(3-hydroxypropanoic acid) (also known as 3,6-diamino-$N^2$,$N^5$-bis(L-serine)-pyrazine-2,5-dicarboxamide),

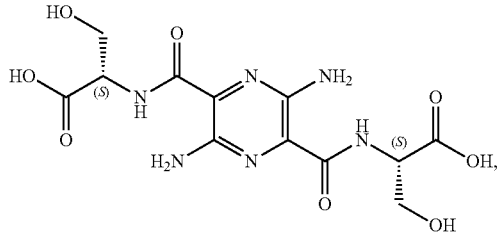

or a pharmaceutically acceptable salt thereof.

In still yet another aspect, the fluorescent GI agent is selected from the group consisting of acridines (for instance and without limitation acridine, acriflavine, acridine orange, acridine yellow, proflavine, aminacrine, enflavine, quinacrine, proflavine hydrochloride, acridine orange, acridine yellow, phenazine, phenosafranin, neutral red, janus green B, phenothiazine, thionin, methylene blue, Azure II, toluidine blue, phenoxathiin, phenoxazine, oxazine 1, cresyl violet perchlorate, nile red, nile blue, or oxazine); acridones (for instance and without limitation, 2-aminoacridone, the acridones disclosed in U.S. Pat. No. 8,034,558 (the contents of which are incorporated herein in their entirety), acridone, and acridanone); anthracenes (for instance and without limitation, anthracene carboxyimide, 2,6,9,10-tetra(p-dibutylaminostyryl)anthracene, and anthroylnitrile); anthracyclines; anthraquinones; azaazulenes and azo azulenes (for instance and without limitation, the aza azulenes and azo azulenes disclosed in US 20120203102 (the contents of which are incorporated herein in their entirety)); benzenes; benzimidazoles; benzofurans; benzoindocarbocyanines; benzoindoles; benzothiophenes; carbazoles; coumarins (for instance and without limitation, coumarin 6, 7-hydroxycoumarin, 7-hydroxycoumarin-3-carboxylic acid, 6,8-difluoro-7-hydroxy-4-methylcoumarin, 7-amino-4-methylcoumarin, coumarin succinimidyl esters, coumarin 4-sulfotetrafluorophenyl esters, coumarin sulfonyl chlorides, coumarin isothiocyanates, coumarin maleimides, 6,8-difluoro-7-hydroxycoumarin; 4-hydroxycoumarin, 7-hydroxy-4-(trifluoromethyl)coumarin, 4-trifluoromethylumbeliferone, 7-methoxycoumarin-4-acetic acid, coumarin 1, coumarin 6, 3-(2-benzimidazolyl)-7-(diethylamino)coumarin, coumarin 30, 7-Amino-4-(trifluoromethyl)coumarin, coumarin 314, and coumarin 343); cyanines (for instance and without limitation, the cyanines disclosed in WO2012054784 (the contents of which are incorporated herein in their entirety), hepatamethine cyanine, indocyanines, tetramethylrhodamine, 1,1'-diethyl-2,2'-cyanine iodide, 1,1'-diethyl-2,2'-carbocyanine iodide, 1,1'-diethyl-2,2'-dicarbocyanine iodide, 1,1'-diethyl-4,4'-cyanine iodide, 1,1'-diethyl-4,4'-carbocyanine iodide, 1,1'-didethyl-4,4'-dicarbocyanine iodide, 3,3'-diethyloxacarbocyanine iodide, 3,3'-diethyloxadicarbocyanine iodide, 3,3'-diethyloxatricarbocyanine iodide, 1,1'-diethyl-3,3,3',3'-tetramethylindocarbocyanine iodide, 1,1'-diethyl-3,3,3',3'-tetramethylindodicarbocyanine iodide, 1,1'-diethyl-3,3,3',3'-tetramethylindotricarbocyanine iodide, indocyanine green, 3,3'-diethylthiacarbocyanine iodide, 3,3'-diethylthiadicarbocyanine iodide, 3,3'-diethylthiatricarbocyanine iodide, merocyanine 540, 4-(dicyanomethylene)-2-methyl-6-(p-dimethyl aminostyryl)-4H-pyran, 3,3'-diethyl-9-methyl-4,5,4',5'-dibenzothiacarbocyanine, or a polymethine chain linked to two nitrogen-containing heterocycles, such as indoles, benzothiazoles, benzoxazoles, quinolones, pyrazoles, pyradines, pyrimidones, or pyrroles); dibenzofurans; dibenzothiophenes; dipyrrolo dyes; flavones; imidazoles; indocarbocyanines; indocyanines; indoles; isoindoles; isoquinolines; naphthacenediones; naphthalenes (for instance and without limitation naphthalimide and naphthaldiimide); naphthoquinones; phenanthrenes; phenanthridines; phenoselenazines; phenothiazines; phenoxazines; phenylxanthenes; polyfluorobenzenes; purines; pyrazines (as disclosed elsewhere herein); pyrazoles; pyridines; pyrimidones; pyrroles; quinones (for instance and without limitation, 1,4-benzoquinone, hydroquinone, 2,3,5,6-tetrachloro-1,4-benzoquinone, tetrachlorohydroquinone, 2,3,5,6-tetramethyl-1,4-benzoquinone, 2,3-dichloro-5,6-dicyano-1,4-benzoquinone, 3,4,5,6-tetrachloro-1,2-benzoquinone, 2,5- diphenyl-1,4-benzoquinone, 2,5-di-tert-butyl-1,4-benzoquinone, tetracyanoethylene, 7,7,8,8-tetracyanoquinodimethane, 1,4-naphthoquinone, 1,4-naphthoquinone-2-sulfonic acid, potassium salt, 2,3-dichloro-1,4-naphthoquinone, 2-methyl-1,4-naphthoquinone, 9,10-phenanthrenequinone, 1,2-naphthoquinone; 1,2-naphthoquinone-4-sulfonic acid, sodium salt, 9,10-anthraquinone, alizarin; alizarin red, 1,4-anthraquinone, 5,12-naphthacenequinone, and 6,13-pentacenequinone); quinolines; quinolones; rhodamines (for instance and without limitation, rhodamine, Rhodamine 6G, Rhodamine B, Rhodamine 123, or Rhodamine 101); squaraines; tetracenes; thiophenes; triphenyl methane dyes; xanthenes (for instance and without limitation, fluorescein, 2',7'-dichlorofluorescein, 3,4,5,6-tetrachlorofluorescein, eosin B, eosin Y, phloxine B, erythrosine B, rose Bengal, xantphos, 4,5-bis(diphenylphosphino)-9,9-dimethylxanthene); xanthones; and derivatives thereof.

In some aspects, the fluorescent GI agent (challenge molecule) that is not substantially absorbed by a healthy gut may comprise a fluorescent dye conjugated to a carbohydrate. In some aspects, the GI agent that is not substantially absorbed by a healthy gut, per se, is fluorescent. In some such aspects, the fluorescent GI agent may be characterized by a molecular weight or molecular weight range. In some aspects, the fluorescent GI agent may be characterized by a molecular weight of about 300, about 310, about 320, about 330, about 340, about 350, about 360, about 370, about 380, about 390, about 400, about 410, about 420, about 430, about 440, about 450, about 460, about 470, about 480, about 490, about 500, or larger, and any range constructed therefrom, such as from about 300 to about 500, from about 300 to about 500, from about 320 to about 450, or from about 340 to about 400.

The composition may include a second fluorescent GI agent, wherein the fluorescent GI agent is substantially absorbed by a healthy gut. The second fluorescent GI agent may be similar to the first fluorescent GI agent, in that it may include a fluorescent dye; however, the second fluorescent GI agent may be designed to be absorbed by the gut. In certain aspects, the second fluorescent GI agent molecule is 3,6-diaminopyrazine-2,5-dicarboxylic acid. In some such aspects, the fluorescent GI agent may be characterized by a molecular weight or molecular weight range. In some aspects, the fluorescent GI agent may be characterized by a molecular weight of about 100, about 110, about 120, about 130, about 140, about 150, about 160, about 170, about 180, about 190, about 200, about 210, about 220, about 230, about 240, or about 250, and any range constructed therefrom, such as from about 100 to about 250, from about 140 to about 220, or from about 150 to about 250.

For compositions comprising a second fluorescent GI agent, the second fluorescent GI agent may possess different photophysical properties from the first fluorescent GI agent. Thus, the two agents display different absorption and emission wavelengths, and allow real-time measurement of uptake and permeability in the gut. In certain embodiments, the second fluorescent GI agent fluoresces at a wavelength different from the first fluorescent GI agent.

Pharmaceutically acceptable salts are known in the art. In any aspect herein, the fluorescent GI agent may be in the form of a pharmaceutically acceptable salt. By way of example and not limitation, pharmaceutically acceptable salts include those as described by Berge, et al. in *J. Pharm. Sci.*, 66(1), 1 (1977), which is incorporated by reference in its entirety for all purposes. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, di succinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, tromethamine, aluminum, calcium, lithium, magnesium, potassium, sodium zinc, barium and bismuth. Any functional group in the fluorescent GI agent capable of forming a salt may optionally form one using methods known in the art. By way of example and not limitation, amine hydrochloride salts may be formed by the addition of hydrochloric acid to the indicator substance. Phosphate salts may be formed by the addition of a phosphate buffer to the indicator substance. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

The fluorescent GI agent may suitably be formulated with one or more pharmaceutically acceptable carriers, adjuvants, and/or excipients and in the form of a capsule, tablet (pill), powder, syrup, dispersion, suspension, emulsion, solution, or the like. Non-limiting examples of suitable liquid carriers include water; saline; aqueous dextrose; glycols; ethanol; oils including those of petroleum, animal, vegetable or synthetic origin; and combinations thereof. Non-limiting examples of suitable pharmaceutical adjuvants/excipients include starch, cellulose, polyvinylpyrrolidone, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The fluorescent GI agent may also be suitably formulated with additional conventional pharmaceutical additives such as preservatives, stabilizing agents, wetting or emulsifying agents, salts for adjusting osmotic pressure, buffers and the like. Such compositions will, in any event, contain an effective amount of the indicator substance so as to prepare the proper dosage form for proper administration to the subject.

The fluorescent GI agent can be administered by any suitable method. The method will be based on the medical needs of the patient and selected by the medical professional prescribing the at home procedure. Examples of administration methods include, but are not limited to, oral or enteral administration. In some embodiments, the fluorescent GI agent is administered via an enteral solution. In yet another embodiment, the fluorescent GI agent is administered by multiple enteral solutions.

As used herein, "enteral administration" refers to any method of administration that delivers a fluorescent GI agent directly or indirectly to the patient using the gastrointestinal tract. Examples of enteral administration include, but are not limited to, oral, sublingual, buccal and rectal. Suitable compositions for oral administration include solid formulations such as tablets, lozenges and capsules, which can contain liquids, gels, or powders. Liquid formulations can include solutions, syrups and suspensions, which may be administered in liquid form or used in soft or hard capsules. Such formulations may include a pharmaceutically acceptable carrier, for example, water, ethanol, polyethylene glycol, cellulose, phosphate-buffered saline (PBS), or an oil. The formulation may also include one or more emulsifying agents and/or suspending agents. Preparation of pharmaceutically acceptable formulations can be accomplished according to methods known in the art.

Compositions and formulations that provide for controlled release of the fluorescent GI agent are within the scope of the present disclosure. Typically, controlled release produces delayed release at a constant release rate, but other controlled release forms can produce non-constant release rates, such as to produce pulses of drug release over a longer period of time. Controlled release compositions may also be formulated to provide for fluorescent GI agent release in the stomach, small intestine (duodenum), large intestine or colon.

Compositions for the controlled release of medicaments are known in the art. Generally, such compositions contain particles comprising a medicament mixed with, or covered by, a coating material that is temporarily resistant to degradation or disintegration in the stomach and/or in the intestine. Release of the medicament may occur by leaching, erosion, rupture, diffusion, or similar actions, depending upon the nature and thickness of the coating material. In some aspects, a medicament is coated onto spherical particles, such as dicalcium phosphate, which are in turn enclosed within gelatin capsules or compressed into tablets. One or more coatings may optionally be applied to the medicament-coated particles. Generally, such coatings are used to improve the stability of the dosage and/or enable enteric release of the medicament.

In some aspects, compositions comprising the fluorescent GI agent can be formulated with an enteric coating that is a polymer barrier and that prevents its dissolution or disintegration in the gastric environment. This provides for fluorescent GI agent release after the stomach, such as in the upper tract of the intestine. An enteric coating may work by presenting a surface that is stable at the intensely acidic pH found in the stomach, but breaks down rapidly at a higher pH (alkaline pH). For example, they will not dissolve in the gastric acids of the stomach (pH ~3), but they will in the alkaline (pH 7-9) environment present in the small intestine. By preventing fluorescent GI agent dissolution in the stomach when the fluorescent GI agent composition reaches the neutral or alkaline environment of the intestine, it can then dissolve and become available for absorption into the bloodstream. Non-limiting examples of suitable enteric coating polymers include shellac, cellulose acetate phthalate, poly (methacrylic acid-co-methyl methacrylate), cellulose acetate trimellitate, poly(vinyl acetate phthalate), hydroxypropyl methylcellulose phthalate.

U.S. Pat. No. 5,968,554 to Beiman, et al. teaches a multi-layered controlled release dosage capable of delivering a medicament to both the stomach and the duodenum. Similarly, U.S. Pat. No. 6,312,728, also to Beiman, et al., teaches a multi-layered controlled release dosage capable of delivering a pharmaceutical to both the duodenum and large intestine or colon or to the stomach, duodenum, and large intestine or colon. Both references are incorporated herein by reference.

Methods of preparing controlled release compositions are known in the art and are within the scope of the present invention, including, for example, conventional pan coating, perforated pan coating, fluidized-bed coating, top-spray coating, bottom-spray coating, and tangential-spray coating. See, e.g., Atul M. Mehta & David M. Jones, Coated Pellets Under the Microscope, PHARM. TECH., June 1985, which is also hereby incorporated by reference. Various excipients, as described elsewhere herein, may be incorporated into the controlled-release compositions.

Examples of sensors (also referred to as a "GI sensor") suitable for use with the methods and devices herein include, but are not limited to, those disclosed in U.S. Pat. Nos. 9,632,094, 10,194,854, 10,548,521, WO 2019/143676, U.S. Ser. No. 16/552,539, U.S. Ser. No. 17/331,341 which are all incorporated by reference in their entirety for all purposes. The sensor comprises at least one radiation source. A radiation source is understood to be any device which can emit radiation anywhere on the electromagnetic spectrum. In some aspects, the electromagnetic radiation is in the visible, infrared, ultraviolet, and/or gamma spectral range. Without restricting the type of radiation used and for convenience only, hereinafter radiation is generally designated as "light" whether or not it is in the visible region of the electromagnetic spectrum, and the radiation source is described more particularly with reference to a "light source". However, other configurations of the radiation source are possible, in some aspects, and it is also possible, in some aspects, to combine different types of radiation sources.

The radiation source can be, for example, an integral constituent of the sensor, for example in the context of a layer construction of the sensor. The radiation source is therefore designed to generate at least one interrogation light directly within the sensor, in contrast to external generation of the interrogation light. Instead of an individual light source, in some aspects, it is also possible to use a plurality of light sources, for example redundant light sources for emitting one and the same wavelength, and/or a plurality of different light sources for emitting different wavelengths. Generally, the at least one light source is designed to irradiate the body surface with at least one interrogation light.

An interrogation light is understood to be a light that can be used for the detection of an fluorescent GI agent as disclosed elsewhere herein, whose light excites the fluorescent GI agent inside a body tissue and/or a body fluid of the patient, for example with variable penetration depth, and causing a perceptible response, more particularly, an optically perceptible response. This excitation takes place in such a way that a luminescence, a fluorescence and/or a phosphorescence is initiated in the fluorescent GI agent. In some aspects, other types of excitation occur, for example scattering of the light at an identical or shifted wavelength. Generally, at least one response light is generated by the fluorescent GI agent in response to the interrogation light.

The interrogation light is designed such that the desired response is excited in a targeted manner in the fluorescent GI agent. Accordingly, by way of example and not limitation, a wavelength and/or a wavelength range of the interrogation light and/or some other property of the interrogation light can be adapted or adjusted based on the identity and properties of the fluorescent GI agent. This can be done directly by the radiation source, for example, by virtue of the radiation source providing the interrogation light having a specific wavelength and/or in a specified wavelength range and/or by the inclusion of at least one excitation filter being used to filter out the desired interrogation light from a primary light of the light source. In some aspects, the sensor performs fluorescence measurements on the indicator substance. Accordingly, the interrogation light can be adapted to the excitation range of the fluorescence of the fluorescent GI agent.

The sensor further comprises at least one detector designed to detect at least one response light incident from the direction of the body surface. The response light can be light in the sense of the above definition. The detector is also an integral constituent of the sensor. The detector is therefore part of the sensor such that the response light is detected directly within the sensor. In some aspects, the detector is configured for diffuse reflection correction such that any light that does not emanate directly from the fluorescent GI agent inside the body of the patient can be either filtered out or corrected by way of background correction.

In some aspects, the response light represents an optical response of the fluorescent GI agent to the incidence of the interrogation light. Accordingly, the detector and/or the detector in interaction with at least one response filter is configured to detect in a targeted manner in the spectral range of the response light. In some aspects, the detector and/or the detector in interaction with the at least one response filter is configured to suppress light outside the spectral range of the response light. In some aspects, the detector and/or the detector in interaction with the at least one response filter can be designed to suppress the interrogation light. In yet another aspect, response filters are designed to suppress the detection of ambient light, particularly at wavelengths that can travel long distances in tissue prior to absorption, such as a spectral range of from about 700 to about 1100 nm. The interrogation light and the response light can be configured such that they are spectrally different or spectrally shifted relative to one another with regard to their spectral intensity distribution.

By way of example and not limitation, in some aspects, the response light shifts toward longer wavelengths in comparison with the interrogation light, which generally occurs in a fluorescence measurement (i.e., the Stokes shift). By way of another example, the Stokes shift of a peak wavelength of the response light relative to a peak wavelength of the interrogation light is between about 10 nm and about 200 nm, more particularly between about 100 nm and about 150 nm, and particularly about 120 nm. The detector and/or the detector in interaction with the at least one response filter can be designed to detect such response light. About in this context means±10 nm.

The at least one radiation source, more particularly, the at least one light source, and the at least one detector are designed to irradiate the body surface with the interrogation light and to detect at least one response light incident from the direction of the body surface. The radiation source and the detector are therefore optically connected to the body surface in such a way that, through the body surface, for example transcutaneously, the interrogation light can be radiated into the body tissue or the body fluid of the patient, and that, likewise through the body surface, for example transcutaneously, the response light from the body tissue or the body fluid is observed by the detector.

In addition to the at least one detector and the at least one radiation source, the sensor assembly may comprise further elements. In some aspects, the sensor comprises further elements. Thus, the sensor can comprise, for example, at least one interface for data exchange. Said data can be, for example, measurement results for intensities of the response light detected by the detector. Data already partly processed, filtered or partly or completely evaluated data, can also be transmitted wirelessly to the computer program on the mobile computing device. In some aspects, transponder technology known in the art may be used, for example, to initiate a measurement via the sensor and/or to interrogate measurement data from the sensor. In some aspects, corresponding radiofrequency readers such as are known from RFID technology (radiofrequency identification label technology), for example, can be used for this purpose. In some aspects, Bluetooth technology is use for this purpose.

In some aspects, a 2-sided adhesive is employed as a constituent part of the sensor. The side facing the skin is selected to adhere reliably to the skin for an extended period of time (e.g., 24 to 48 hrs.), even in the presence of moisture, such as sweat. In some aspects, an acrylate-based adhesive is used for bonding to the skin. In yet another aspect, the skin is pre-treated with a barrier film, such as by application of rapidly-drying liquid film that upon drying forms a "second skin". In such aspects the barrier film aids in the long-term, reliable attachment of the acrylate-based adhesive to the skin, while also having the benefit of allowing sensor removal without disruption or removal of the skin epidermis. In some aspects, the barrier film is CAVILON™ (manufactured by 3M). The second side of the adhesive, which faces towards the sensor, may be selected to adhere as strongly as desired to the face of the sensor. In one such aspect the sensor face is constructed from a polymer material, such as MAKROLON™, and the adhesive is rubber based. One non-limiting example of an appropriate 2-sided adhesive is 3M product #2477 (Double-Coated TPE Silicone Acrylate Medical Tape with Premium Liner).

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

Examples of methods that may incorporate the use of the mobile computing device herein include, but are not limited to, those disclosed in US20150147277 and Richard B. Dorshow, et al., "Transdermal fluorescence detection of a dual fluorophore system for noninvasive point-of-care gastrointestinal permeability measurement," Biomedical Optics Express, Vol. 10, No. 10/1 Oct. 2019, which discloses methods that enable a specimen-free, noninvasive, point-of-care gastrointestinal permeability measurement translatable to human clinical use, both of which are incorporated by reference in their entirety for all purposes. In yet another method, (2R,2'R)-2,2'-((3,6-diaminopyrazine-2,5-dicarbonyl)bis(azanediyl))bis(3-hydroxypropanoic acid) (also known as MB-102) is administered orally to a patient after a sensor is placed on the body of patient. Transdermal fluorescence detection is initiated to detect baseline fluorescence before delivery of MB-102, and is monitored continuously after oral administration throughout the measurement.

GI function may suitably be measured by administering a composition comprising the fluorescent GI agent (indicator substance) to a subject (e.g., a patient). The fluorescent GI agent substance is absorbed by the gut of the subject, is irradiated with non-ionizing radiation having a wavelength of at least 350 nm, and is detected in the subject's skin, blood, urine, or fascia. In some embodiments, the absorbed fluorescent GI agent is irradiated and detected transcutaneously. In certain embodiments, the detected fluorescence of the GI agent is measured over time.

The methods of the present disclosure may also provide an assessment of the location of a gut disease or an injury. In such embodiments, an effective amount of a composition containing a fluorescent GI agent that is not substantially absorbed by a healthy gut is administered to the patient, and a second fluorescent GI agent that is substantially absorbed by a healthy gut is administered to the patient. The composition is irradiated with non-ionizing radiation thereby causing it to fluoresce. The fluorescence of each GI agent may be detected and measured over time and the location of disease or injury in the gut of the subject may be assessed based on the time period between the detected fluorescence of each GI agent and administration. The two fluorescent GI agents may possess different photophysical properties allowing for the simultaneous measurement of the fluorescence the two molecules.

In some such embodiments, the detected fluorescence of the fluorescent GI agent that is not substantially absorbed by a healthy gut may occur before or substantially simultaneously as compared the detected fluorescence of the GI agent that is substantially absorbed by a healthy gut thereby indicating that the disease or injury is located in the proximal portion of the gut. In particular embodiments, this may indicate the subject is suffering from Celiac disease.

In some such embodiments, the detected fluorescence of the fluorescent that is not substantially absorbed by a healthy gut may occur substantially later in time as compared the detected fluorescence of the fluorescent that is substantially absorbed by a healthy gut thereby indicating that the disease or injury is located in the distal portion of the gut. In particular embodiments, this may indicate the subject is suffering from ulcerative colitis.

In some embodiments, the method provides for an assessment of the size of the gut openings in a patient. Such embodiments may comprise the steps of: administering an effective amount of a composition comprising at least two fluorescent GI agents, wherein each fluorescent GI agent has a different size, and is absorbed by a healthy gut to a different degree into the subject's gut; irradiating the composition with non-ionizing radiation, wherein the radiation causes the GI agents to fluoresce; detecting the fluorescence of each fluorescent GI agent in the composition; and assessing the size of the openings within the subject's gut, based on the size of each fluorescent GI agent. For instance, a first fluorescent GI agent that is not substantially absorbed by a healthy gut and having a defined molecular weight and a second fluorescent GI agent that is not substantially absorbed by a healthy gut and having a defined molecular weight different that the first fluorescent GI agent, and further wherein the first and second fluorescent GI agents have different photophysical properties, are administered to a patient. The relative amount of the absorbed fluorescent GI agents can be detected and quantified and correlated with a molecular weight and concomitant size of the gut opening. This method is also suitable for three or more fluorescent GI agents having different molecular weights.

The patent claims at the end of this document are not intended to be construed under 35 U.S.C. § 112(f) unless traditional means-plus-function language is expressly recited, such as "means for" or "step for" language being expressly recited in the claim(s). A method recited herein may comprise one or more steps, without being construed under 35 U.S.C. § 112 (f).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-transitory computer-readable media having computer-executable instructions thereon, wherein when executed by at least one processor of a mobile computing device, cause the at least one processor of the mobile computing device to:
    wirelessly communicatively couple the mobile computing device to a sensor;
    display a sensor placement screen that instructs a user to place the sensor on a body of a patient;
    display a customization screen that instructs the user to initiate customization of the sensor to a skin tone of the patient;
    upon initiation of the customization of the sensor,
        collect a background level of light absorbance that naturally emanates from the body of the patient for customization of the sensor; and
        adjust a light strength or a detector sensitivity in the sensor to account for differing skin colors of different patients;
    prompt the user to administer a fluorescent gastrointestinal (GI) agent into the body of the patient;
    transmit a signal from the mobile computing device to the sensor to cause the sensor to initiate collection of light absorbance data for calculating a GI function measurement of the patient;
    receive light absorbance data from the sensor; and
    store the received light absorbance data.

2. The non-transitory computer readable media of claim 1, wherein to prompt the user to administer the fluorescent GI agent, the computer-executable instructions cause the at least one processor of the mobile computing device to display an administration screen that instructs the user to administer the fluorescent GI agent.

3. The non-transitory computer readable media of claim 1, wherein to prompt the user to administer the fluorescent GI agent, the computer-executable instructions cause the at least one processor of the mobile computing device to vibrate the mobile computing device.

4. The non-transitory computer readable media of claim 1, wherein to prompt the user to administer the fluorescent GI agent, the computer-executable instructions cause the at least one processor of the mobile computing device to transmit a control signal from the mobile computing device to the sensor to cause the sensor to generate an audible, visual, or haptic alert that prompts the user to administer the fluorescent GI agent.

5. The non-transitory computer-readable media of claim 1, wherein the computer-executable instructions further cause the processor of the mobile computing device to:
    calculate the GI function measurement of the patient using the light absorbance data.

6. The non-transitory computer-readable media of claim 5, wherein the computer-executable instructions further cause the processor of the mobile computing device to:

wirelessly transmit the GI function measurement of the patient to a computing device of a health care provider.

7. The non-transitory computer-readable media of claim 1, wherein the computer-executable instructions further cause the processor of the mobile computing device to:
display an error message if an error occurs during execution of the instructions.

8. The non-transitory computer-readable media of claim 1, wherein the at least one processor of the mobile computing device displays a pairing screen on the mobile computing device that instructs a user to wirelessly communicatively couple the mobile computing device to a sensor.

9. A computer-implemented method for assessing gastrointestinal (GI) function in a patient in need thereof, the method implemented using a mobile computing device that comprises at least one processor in communication with at least one memory, and at least one user interface, the method comprising:
displaying a sensor placement screen that instructs a user to place a sensor on the body of a patient;
communicatively coupling the sensor on the body of the patient to the mobile computing device;
displaying a customization screen that instructs the user to initiate customization of the sensor to a skin tone of the patient;
upon initiation of the customization of the sensor,
collecting a background level of light absorbance that naturally emanates from the body of the patient for customization of the sensor; and
adjusting a light strength or a detector sensitivity in the sensor to account for differing skin colors of different patients;
prompting the user to administer a fluorescent GI agent into the body of the patient;
transmitting a signal from the mobile computing device to the sensor, the signal causing the sensor to initiate collection of light absorbance data; and
displaying a measurement screen that instructs the user to wait a predetermined period of time while the sensor collects the light absorbance data.

10. The computer-implemented method according to claim 9, wherein the method further comprises:
displaying the customization screen that instructs the user on how to customize the sensor prior to initiating collection of light absorbance data.

11. The computer-implemented method according to claim 9, wherein the method further comprises:
calculating the GI function of the patient using the light absorbance data.

12. The computer-implemented method according to claim 11, wherein the method further comprises:
displaying a results screen that displays the calculated GI function of the patient.

13. The computer-implemented method according to claim 11, wherein the method further comprises:
transmitting from the mobile computing device to a computing device of a health care provider the calculated GI function measurement, the light absorbance data, or both.

14. The computer-implemented method according to claim 9, wherein the method further comprises:
receiving patient/user input after each step in the computer implemented method, the patient/user input indicating that the step was successfully completed.

15. The computer-implemented method according to claim 9, wherein the method further comprises:
providing feedback to the user and/or patient if an error occurs at any time during execution of the method.

16. A system for assessing gastrointestinal (GI) function in a patient in need thereof, the system comprising:
a mobile computing device having installed thereon a computer program for assisting a user in assessing GI function in the patient;
a sensor configured to be wirelessly communicatively coupled to the mobile computing device, wherein the sensor is configured to be customized to a skin tone of the patient; and
a fluorescent GI agent;
wherein the mobile computing device is configured to:
cause customization of the sensor by,
collecting a background level of light absorbance that naturally emanates from the body of the patient for customization of the sensor; and
adjusting a light strength or a detector sensitivity in the sensor to account for differing skin colors of different patients; and
transmit a signal to the sensor, the signal causing the sensor to initiate collection of light absorbance data.

17. The system according to claim 16, wherein the computer program on the mobile computing device is further configured to calculate the GI function of the patient using light absorbance data collected by the sensor.

18. A kit for gastrointestinal (GI) function assessment of a patient, the kit comprising:
a fluorescent GI agent configured to:
emit at least one response light in response to electromagnetic radiation generated by a sensor;
the sensor configured to:
attach to the body of a patient;
emit electromagnetic radiation in a direction of the body of the patient; and
detect at least one response light emitted by the fluorescent GI agent inside the body of the patient in response to the electromagnetic radiation; and
a mobile computing device wirelessly communicatively coupled to the sensor and configured to:
transmit a first signal to the sensor, the first signal causing the sensor to initiate customization of the sensor to a skin tone of the patient;
upon initiation of the customization of the sensor,
collect a background level of light absorbance that naturally emanates from the body of the patient for customization of the sensor; and
adjust a light strength or a detector sensitivity in the sensor to account for differing skin colors of different patients;
transmit a second signal to the sensor, the second signal causing the sensor to initiate collection of light absorbance data;
receive response light data from the sensor; and
calculate the GI function of the patient based on the response light data.

19. The kit according to claim 18, further comprising:
written instructions describing how to use the fluorescent GI agent and the sensor of the kit in order to assess the GI function of the patient.

* * * * *